(12) United States Patent  
Bond et al.

(10) Patent No.: US 8,825,170 B2
(45) Date of Patent: Sep. 2, 2014

(54) LOW-POWER SYSTEM CLOCK CALIBRATION BASED ON A HIGH-ACCURACY REFERENCE CLOCK

(75) Inventors: Matthew Bond, Tempe, AZ (US); Charles R. Gordon, Phoenix, AZ (US); Weizheng Liang, Chandler, AZ (US); James D. Reinke, Maple Grove, MN (US); Jonathan P. Roberts, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 746 days.

(21) Appl. No.: 12/915,832

(22) Filed: Oct. 29, 2010

(65) Prior Publication Data

US 2012/0109259 A1    May 3, 2012

(51) Int. Cl.
*A61N 1/00* (2006.01)
*A61N 1/08* (2006.01)
*A61N 1/02* (2006.01)
*G06F 1/12* (2006.01)
*A61N 1/372* (2006.01)

(52) U.S. Cl.
CPC .............. *A61N 1/08* (2013.01); *A61N 1/37276* (2013.01); *A61N 1/025* (2013.01); *G06F 1/12* (2013.01); *A61N 1/372* (2013.01)
USPC .......................................................... 607/60

(58) Field of Classification Search
CPC ........................... A61N 1/025; A61N 1/37252
USPC ................... 607/27, 60, 16; 600/509
See application file for complete search history.

(56) References Cited

U.S. PATENT DOCUMENTS

| | | | |
|---|---|---|---|
| 5,022,395 A * | 6/1991 | Russie | ............................. 607/16 |
| 6,009,319 A | 12/1999 | Khullar et al. | |
| 7,139,613 B2 | 11/2006 | Reinke et al. | |
| 7,474,914 B2 * | 1/2009 | Barr | .............................. 600/509 |
| 2003/0056135 A1 | 3/2003 | Splett et al. | |
| 2004/0133390 A1 | 7/2004 | Osorio et al. | |
| 2004/0215272 A1 | 10/2004 | Haubrich et al. | |

OTHER PUBLICATIONS

International Preliminary Report on Patentability from international application No. PCT/US2011/034249, dated May 10, 2013, 7 pp.
International Search Report and Written Opinion of international application No. PCT/US2011/034249, dated Sep. 6, 2011, 10 pp.

* cited by examiner

*Primary Examiner* — Christopher D Koharski
*Assistant Examiner* — Philip Edwards
(74) *Attorney, Agent, or Firm* — Evans M. Mburu

(57) ABSTRACT

Various techniques are described for periodically performing a calibration routine to calibrate a low-power system clock within an implantable medical device (IMD) based on a high accuracy reference clock also included in the IMD. The system clock is powered continuously, and the reference clock is only powered on during the calibration routine. The techniques include determining a clock error of the system clock based on a difference between frequencies of the system clock and the reference clock over a fixed number of clock cycles, and adjusting a trim value of the system clock to compensate for the clock error. Calibrating the system clock with a delta-sigma loop, for example, reduces the clock error over time. This allows accurate adjustment of the system clock to compensate for errors due to trim resolution, circuit noise and temperature.

14 Claims, 12 Drawing Sheets

LOW-POWER SYSTEM CLOCK CALIBRATION BASED ON A HIGH-ACCURACY REFERENCE CLOCK

TECHNICAL FIELD

This disclosure relates to implantable medical devices and, more particularly, to clocking systems of implantable medical devices.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient. Some medical devices may be "leadless" and include one or more electrodes on an outer housing of the medical device to deliver therapeutic electrical signals to organs or tissues and/or sense intrinsic electrical signals or physiological parameters of a patient.

Medical leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry such as signal generation and/or sensing circuitry. In some cases, the medical leads and the medical device housing are implantable within the patient, while in other cases percutaneous leads may be implanted and connected to a medical device housing outside of the patient. Medical devices with a housing configured for implantation within the patient may be referred to as implantable medical devices. Leadless medical devices are typically implantable medical devices positioned within or adjacent to organs or tissues within a patient for delivery of therapeutic electrical signals or sensing. In some example, leadless implantable medical devices may be anchored to a wall of an organ or to tissue via a fixation mechanism.

Implantable cardiac pacemakers or cardioverter-defibrillators, for example, provide therapeutic electrical signals to the heart, e.g., via electrodes carried by one or more medical leads or via electrodes on an outer housing of a leadless implantable medical device. The therapeutic electrical signals may include pulses for pacing, or shocks for cardioversion or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

In general, implantable medical devices require a small housing form factor to enable an unobtrusive implantation within a patient. In the case of leadless implantable medical devices, the housing form factor must be extremely small to enable implantation within or adjacent to organs or tissue. For example, a leadless pacemaker may be implanted directly into a ventricle of the heart. Battery usage is always a concern when designing implantable medical devices, but this concern is increased for small form factor devices that can only accommodate a small battery canister. A competing design requirement for implantable medical devices is high accuracy clocks that use a substantial amount of current. High clocking accuracy is needed to ensure accurate sensing and delivery of therapeutic electrical signals. Low-power clocks are too inaccurate due to poor long-term stability, temperature characteristics, and trim resolution to meet these requirements.

SUMMARY

In general, this disclosure describes techniques for periodically performing a calibration routine to calibrate a low-power system clock within an implantable medical device (IMD) based on a high accuracy reference clock also included in the IMD. The low-power system clock is powered continuously and controls operation of the IMD, and the high accuracy reference clock is only powered on during the calibration routine to correct inaccuracies of the system clock. The techniques disclosed herein may be employed within an IMD, such as an implantable pacemaker or an implantable leadless pacemaker, to reduce current drain by the clocking system of the IMD.

The techniques include powering on the reference clock at the start of the calibration routine, determining a clock error of the system clock based on a difference between the frequencies of the system clock and the reference clock over a fixed number of clock cycles of the system clock, adjusting a trim value of the system clock to compensate for the clock error, and disabling the reference clock at an end of the calibration routine. In some examples, the calibration routine may be performed with a delta-sigma loop, which includes integrating the clock error over time to calculate a cumulative clock error of the system clock, and adjusting the trim value of the system based on the magnitude and sign of the cumulative clock error. Calibrating the system clock with a delta-sigma loop reduces the clock error over time. This allows accurate adjustment of the system clock to compensate for errors due to trim resolution, circuit noise and temperature. Similar techniques described in this disclosure may be used to calibrate other clocks included in an IMD, such as a telemetry polling clock and a telemetry linking clock used to operate a telemetry module of the IMD.

In one example, the disclosure is directed to an IMD that includes a processor, a system clock that comprises a low power oscillator, according to which the processor operates the IMD, a reference clock that comprises a high accuracy oscillator, and a clock calibrator that periodically performs a calibration routine to calibrate the system clock based on the reference clock, wherein the system clock is continuously powered and the reference clock is powered during the calibration routine.

In another example, the disclosure is directed to a method, which includes operating an IMD in accordance with a system clock that comprises a low power oscillator clock included in the IMD, and periodically performing a calibration routine to calibrate the system clock based on the reference clock, wherein the system clock is continuously powered and the reference clock is powered during the calibration routine.

In a further example, the disclosure is directed to an IMD comprising a system clock that comprises a low power oscillator, a reference clock that comprises a high accuracy oscillator, means for operating the IMD in accordance with the system clock, and means for periodically performing a calibration routine to calibrate the system clock based on the reference clock, wherein the system clock is continuously powered and the reference clock is powered during the calibration routine.

In another example, the disclosure is directed to a computer-readable storage medium comprising instructions that, when executed, cause a programmable processor to operate an IMD in accordance with a system clock that comprises a low power oscillator clock included in the IMD, and periodically perform a calibration routine to calibrate the system clock based on the reference clock, wherein the system clock is continuously powered and the reference clock is powered during the calibration routine.

The details of one or more aspects of the disclosure are set forth in the accompanying drawings and the description below. Other features, objects, and advantages of the disclosure will be apparent from the description and drawings, and from the claims.

DETAILED DESCRIPTION

Figure 1:
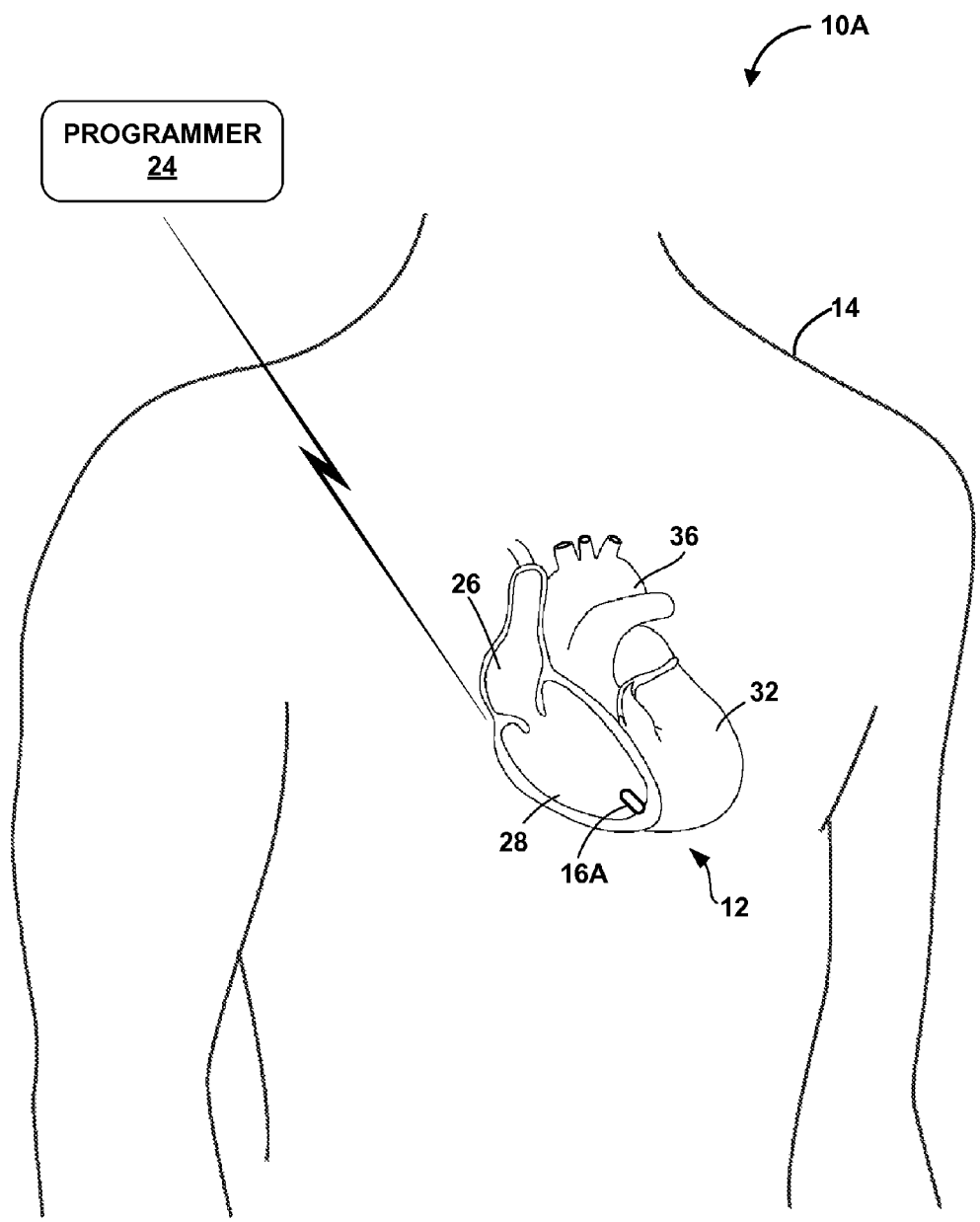
FIG. 1 is a conceptual diagram illustrating an example therapy system comprising a leadless implantable medical device (IMD) that may be used to monitor one or more physiological parameters of a patient and/or provide therapy to the heart of a patient.

In general, this disclosure describes techniques for periodically performing a calibration routine to calibrate a low-power system clock within an implantable medical device (IMD) based on a high accuracy reference clock also included in the IMD. The low-power system clock is powered continuously and controls operation of the IMD, and the high accuracy reference clock is only powered on during the calibration routine to correct inaccuracies of the system clock.

The techniques include powering on the reference clock at the start of the calibration routine, determining a clock error of the system clock based on a difference between the frequencies of the system clock and the reference clock over a fixed number of clock cycles of the system clock, adjusting a trim value of the system clock to compensate for the clock error, and disabling the reference clock at an end of the calibration routine. In some examples, the calibration routine may be performed with a delta-sigma loop, which includes integrating the clock error over time to calculate a cumulative clock error of the system clock, and adjusting the trim value of the system based on the magnitude and sign of the cumulative clock error. Calibrating the system clock with a delta-sigma loop reduces the clock error over time. This allows accurate adjustment of the system clock to compensate for errors due to trim resolution, circuit noise and temperature.

The techniques allow the use a low power oscillator to act as the system clock for the IMD. A high accuracy oscillator may then be used as a reference clock that is turned on periodically for short periods of time to perform calibration to correct the inaccuracies of the system clock. As an example, the reference clock may be turned on for approximately 2-3 seconds for each calibration period of approximately 15 minutes to perform the calibration routine. The techniques disclosed herein may be employed within an IMD, such as an implantable pacemaker or an implantable leadless pacemaker, to reduce current drain by the clocking system of the IMD. In one example, the techniques may reduce total clocking system current drain (including the system clock, the reference clock, and the calibration circuitry) in an IMD to less than 60 nanoamperes (nA).

Similar techniques described in this disclosure may be used to calibrate other clocks included in an IMD, such as a telemetry polling clock and a telemetry linking clock used to operate a telemetry module of the IMD. For example, the techniques may include periodically performing a calibration routine to calibrate a telemetry polling clock, according to which the telemetry module monitors for a telemetry downlink. In some examples, the telemetry polling clock and the system clock may be simultaneously calibrated based on the reference clock. In some cases, the clocks may be simultaneously calibrated with two separate delta-sigma loops.

As another example, the techniques may include performing a calibration routine to calibrate a telemetry linking clock, according to which the telemetry module performs a telemetry session. In this case, the reference clock is powered on during the telemetry session such that the telemetry linking clock may be continuously calibrated based on the reference clock during the telemetry session. Performing telemetry with, e.g., an external programmer of the IMD, requires extremely high clocking accuracy. In some examples, the telemetry linking clock may be calibrated with another delta-sigma loop.

FIG. 1 is a conceptual diagram illustrating an example therapy system 10A that may be used to monitor one or more physiological parameters of patient 14 and/or to provide therapy to heart 12 of patient 14. Therapy system 10A includes an implantable medical device (IMD) 16A, which is coupled to programmer 24. IMD 16A may be an implantable leadless pacemaker that provides electrical signals to heart 12 via one or more electrodes (not shown in FIG. 1) on its outer housing. Additionally or alternatively, IMD 16A may sense electrical signals attendant to the depolarization and repolarization of heart 12 via electrodes on its outer housing. In some examples, IMD 16A provides pacing pulses to heart 12 based on the electrical signals sensed within heart 12. Patient 14 is ordinarily, but not necessarily, a human patient.

In the example of FIG. 1, IMD 16A is positioned wholly within heart 12 with one end proximate to the apex of right ventricle 28 to provide right ventricular (RV) pacing. Although IMD 16A is shown within heart 12 and proximate to the apex of right ventricle 28 in the example of FIG. 1, IMD 16A may be positioned at any other location outside or within heart 12. For example, IMD 16A may be positioned outside or within right atrium 26, left atrium 36, and/or left ventricle 32, e.g., to provide right atrial, left atrial, and left ventricular pacing, respectively. Depending in the location of implant, IMD 16A may include other stimulation functionalities. For example, IMD 16A may provide atrioventricular nodal stimulation, fat pad stimulation, vagal stimulation, or other types of neurostimulation. In other examples, IMD 16A may be a monitor that senses one or more parameters of heart 12 and may not provide any stimulation functionality. In some examples, system 10A may include a plurality of leadless IMDs 16A, e.g., to provide stimulation and/or sensing at a variety of locations.

IMD 16A includes a system clock (not shown in FIG. 1), according to which it performs sensing and therapy delivery. In order to reduce current drain by the clocking system within IMD 16A, a low-power oscillator may be selected as the system clock. Low-power oscillators, however, suffer from inaccuracies due to poor long-term stability, temperature characteristics, and trim resolution. According to the techniques of this disclosure, IMD 16A includes calibration circuitry that periodically performs a calibration routine to calibrate the low-power system clock based on a high accuracy reference clock also included in IMD 16A. The low-power system clock may be powered continuously to control operation of IMD 16A, and the high accuracy reference clock may be powered only during the calibration routine to correct inaccuracies of the system clock. In this way, the techniques may reduce total clocking system current drain (including the system clock, the reference clock, and the calibration circuitry) in IMD 16A to less than 60 nA.

FIG. 1 further depicts programmer 24 in communication with IMD 16A. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16A. For example, the user may interact with programmer 24 to retrieve physiological or diagnostic information from IMD 16A. A user may also interact with programmer 24 to program IMD 16A, e.g., select values for operational parameters of the IMD 16A. For example, the user may use programmer 24 to retrieve information from IMD 16A regarding the rhythm of heart 12, trends therein over time, or arrhythmic episodes.

In some examples, the user of programmer 24 may receive an alert that a mechanical sensing channel has been activated to identify cardiac contractions in response to a detected failure of an electrical sensing channel. The alert may include an indication of the type of failure and/or confirmation that the mechanical sensing channel is detecting cardiac contractions. The alert may include a visual indication on a user interface of programmer 24. Additionally or alternatively, the alert may include vibration and/or audible notification.

As another example, the user may use programmer 24 to retrieve information from IMD 16A regarding other sensed physiological parameters of patient 14 or information derived from sensed physiological parameters, such intracardiac or intravascular pressure, activity, posture, respiration, tissue perfusion, heart sounds, cardiac electrogram (EGM), intracardiac impedance, or thoracic impedance. In some examples, the user may use programmer 24 to retrieve information from IMD 16A regarding the performance or integrity of IMD 16A or other components of system 10A, or a power source of IMD 16A. As another example, the user may interact with programmer 24 to program, e.g., select parameters for, therapies provided by IMD 16A, such as pacing and, optionally, neurostimulation.

IMD 16A and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16A implant site in order to improve the quality or security of communication between IMD 16A and programmer 24.

Figure 2:
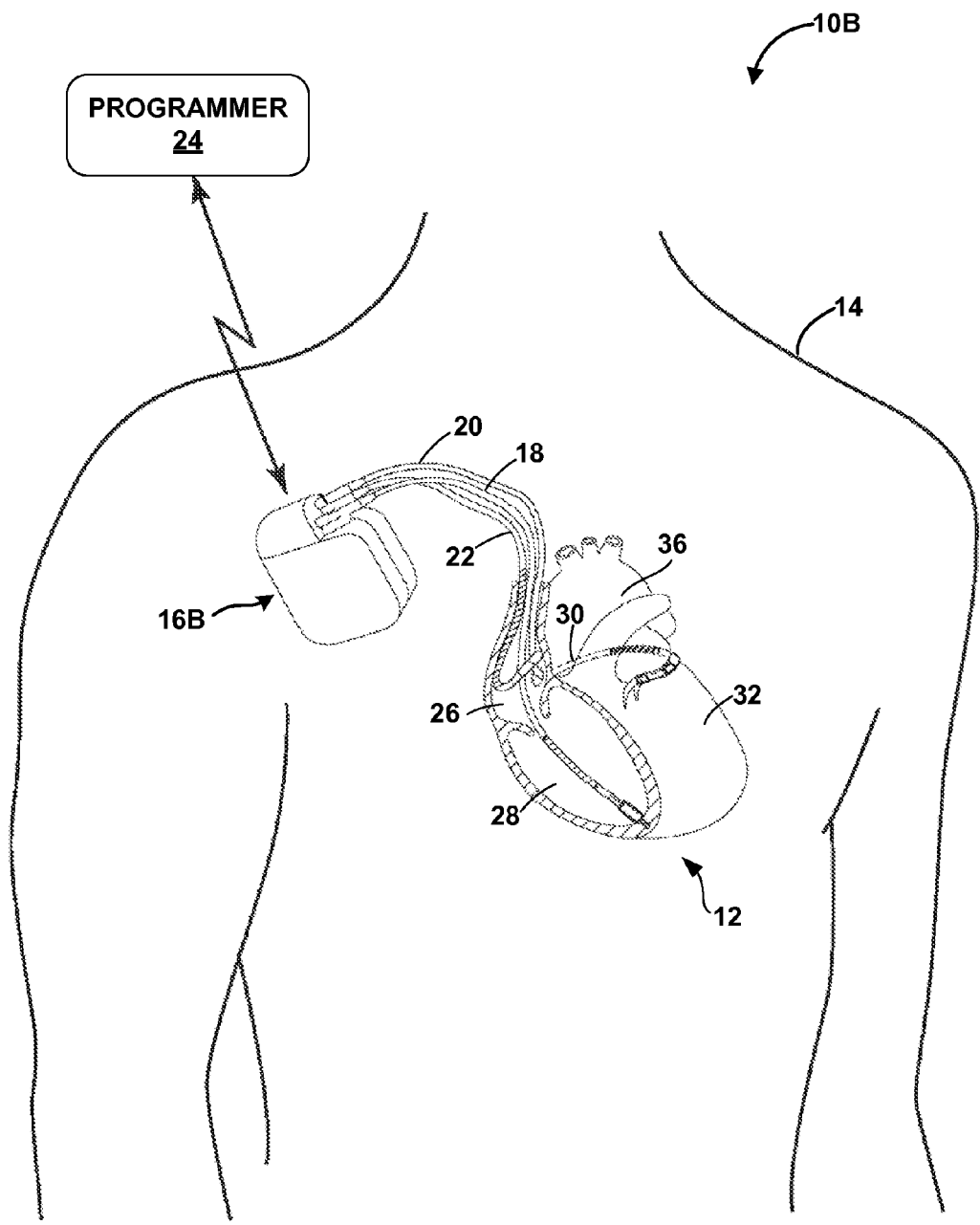
FIG. 2 is a conceptual diagram illustrating another example therapy system comprising an IMD coupled to a plurality of leads that may be used to monitor one or more physiological parameters of a patient and/or provide therapy to the heart of a patient.

FIG. 2 is a conceptual diagram illustrating another example therapy system 10B that may be used to monitor one or more physiological parameters of patient 14 and/or to provide therapy to heart 12 of patient 14. Therapy system 10B includes IMD 16B, which is coupled to leads 18, 20, and 22, and programmer 24. In one example, IMD 16B may be an implantable pacemaker that provides electrical signals to heart 12 via electrodes coupled to one or more of leads 18, 20, and 22. In addition to pacing therapy, IMD 16B may deliver neurostimulation signals. In some examples, IMD 16B may also include cardioversion and/or defibrillation functionalities. In other examples, IMD 16B may not provide any stimulation functionalities and, instead, may be a dedicated monitoring device. Patient 14 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 2, right ventricular (RV) lead 18 extends through one or more veins (not shown), the superior vena cava (not shown), right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12. Right atrial (RA) lead 22 extends through one or more veins and the vena cava, and into the right atrium 26 of heart 12. RA lead 22 may be used to deliver RA pacing to heart 12.

In some examples, system 10B may additionally or alternatively include one or more leads or lead segments (not shown in FIG. 2) that deploy one or more electrodes within the vena cava or other vein, or within or near the aorta. Furthermore, in another example, system 10B may additionally or alternatively include one or more additional intravenous or extravascular leads or lead segments that deploy one or more electrodes epicardially, e.g., near an epicardial fat pad, or proximate to the vagus nerve. In other examples, system 10B need not include one of ventricular leads 18 and 20.

IMD 16B may sense electrical signals attendant to the depolarization and repolarization of heart 12 via electrodes (described in further detail with respect to FIG. 4) coupled to at least one of the leads 18, 20, 22. In some examples, IMD 16B provides pacing pulses to heart 12 based on the electrical signals sensed within heart 12. The configurations of electrodes used by IMD 16B for sensing and pacing may be unipolar or bipolar.

IMD 16B may also provide neurostimulation therapy, defibrillation therapy and/or cardioversion therapy via electrodes located on at least one of the leads 18, 20, 22. For example, IMD 16B may deliver defibrillation therapy to heart 12 in the form of electrical pulses upon detecting ventricular fibrillation of ventricles 28 and 32. In some examples, IMD 16B may be programmed to deliver a progression of therapies, e.g., pulses with increasing energy levels, until a fibrillation of heart 12 is stopped. As another example, IMD 16B may deliver cardioversion or ATP in response to detecting ventricular tachycardia, such as tachycardia of ventricles 28 and 32.

IMD 16B includes a system clock (not shown in FIG. 2), according to which it performs sensing and therapy delivery. In order to reduce current drain by the clocking system within IMD 16B, a low-power oscillator may be selected as the system clock. Low-power oscillators, however, suffer from inaccuracies due to poor long-term stability, temperature characteristics, and trim resolution. According to the techniques of this disclosure, IMD 16B includes calibration circuitry that periodically performs a calibration routine to calibrate the low-power system clock based on a high accuracy reference clock also included in IMD 16B. The low-power system clock may be powered continuously to control operation of IMD 16B, and the high accuracy reference clock may be powered only during the calibration routine to correct inaccuracies of the system clock. In this way, the techniques may reduce total clocking system current drain (including the system clock, the reference clock, and the calibration circuitry) in IMD 16B to less than 60 nA.

As described above with respect to IMD 16A of FIG. 1, programmer 24 may also be used to communicate with IMD 16B. In addition to the functions described with respect to IMD 16A of FIG. 1, a user may use programmer 24 to retrieve information from IMD 16B regarding the performance or integrity of leads 18, 20 and 22 and may interact with programmer 24 to program, e.g., select parameters for, any additional therapies provided by IMD 16B, such as cardioversion and/or defibrillation.

Figure 3:
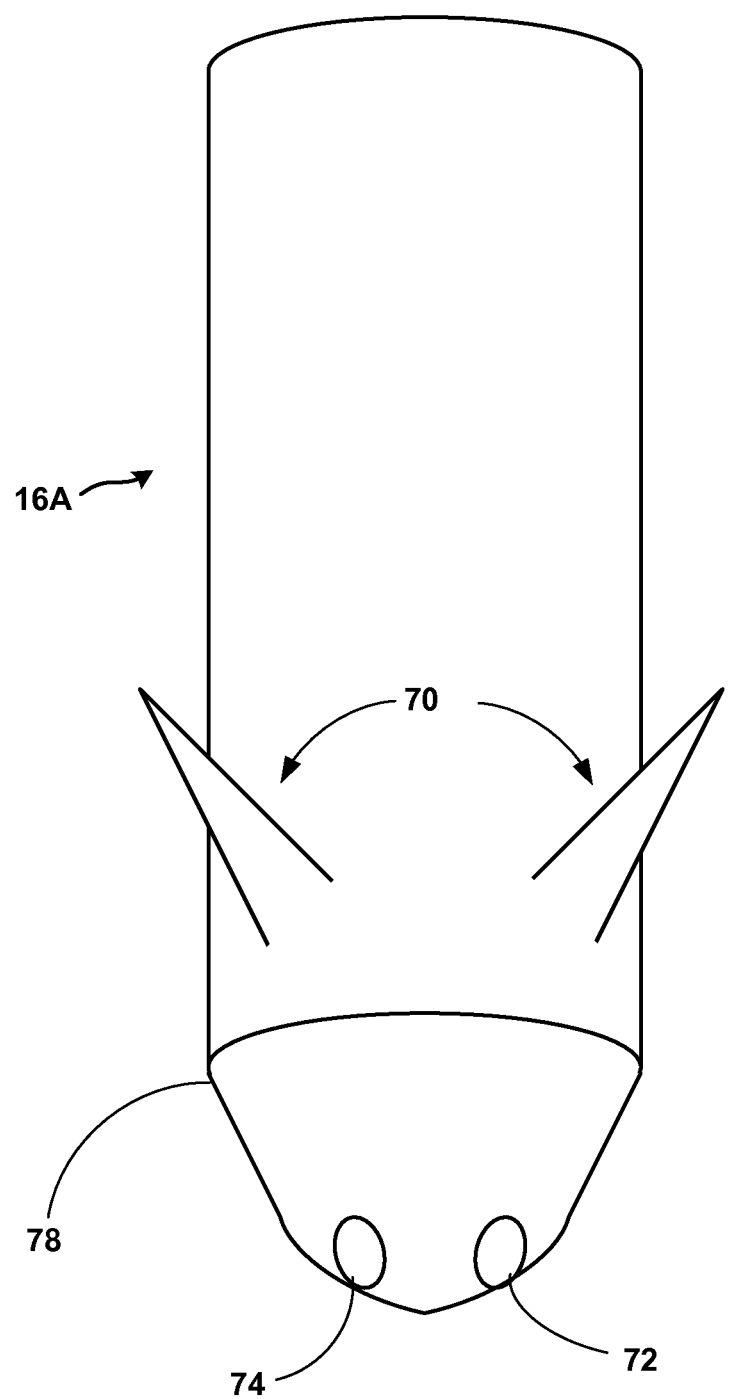
FIG. 3 is a conceptual diagram illustrating the leadless IMD of FIG. 1 in further detail.

FIG. 3 is a conceptual diagram illustrating leadless IMD 16A of FIG. 1 in further detail. In the example of FIG. 3, leadless IMD 16A includes fixation mechanism 70. Fixation mechanism 70 may anchor leadless IMD 16A to a wall of heart 12. For example, fixation mechanism 70 may take the form of multiple tines that may be inserted into a wall of heart 12 to fix leadless IMD 16A at the apex of right ventricle 28. Alternatively, other structures of fixation mechanism 70, e.g., adhesive, sutures, or screws may be utilized. In some examples, fixation mechanism is conductive and may be used as an electrode, e.g., to deliver therapeutic electrical signals to heart 12 and/or sense intrinsic depolarizations of heart 12.

Leadless IMD 16A may also include electrodes 72 and 74 at a tip of outer housing 78. Electrodes 72 and 74 may be used to deliver therapeutic electrical signals to heart 12 and/or sense intrinsic depolarizations of heart 12. Electrodes 72 and 74 may be formed integrally with an outer surface of hermetically-sealed housing 78 of IMD 16A or otherwise coupled to housing 78. In this manner, electrodes 72 and 74 may be referred to as housing electrodes. In some examples, housing electrodes 72 and 74 are defined by uninsulated portions of an outward facing portion of housing 78 of IMD 16A. Other division between insulated and uninsulated portions of housing 78 may be employed to define a different number or configuration of housing electrodes. For example, in an alternative configuration, IMD 16A may include a single housing electrode that comprises substantially all of housing 78, and may be used in combination with an electrode formed by fixation mechanism 70 for sensing and/or delivery of therapy.

Leadless IMD 16A also includes a clocking system (not shown in FIG. 3) that includes a system clock, a reference clock, and calibration circuitry. The system clock, according to which leadless IMD 16A performs sensing and therapy delivery, may be a low-power oscillator that suffers from inaccuracies due to poor long-term stability, temperature characteristics, and trim resolution. The reference clock may be a high accuracy oscillator, such as a crystal oscillator, that runs on a substantial amount of current, e.g., between 0.5 and 1 microampere ($\mu A$). The calibration circuitry periodically performs a calibration routine to calibrate the system clock based on the reference clock. The system clock may be powered continuously to control operation of leadless IMD 16A, but the reference clock may be powered only during the calibration routine to correct inaccuracies of the system clock.

The calibration circuitry may perform the calibration routine according to a calibration period. For example, the calibration circuit may power on the reference clock for approximately 2-3 seconds for each calibration period of approximately 15 minutes to perform the calibration routine. In this way, the total clocking system current drain (including the system clock, the reference clock, and the calibration circuitry) in leadless IMD 16A may be reduced to less than 60 nA.

The calibration circuitry performs the calibration routine by powering on the reference clock at the start of the calibration routine, determining a clock error of the system clock based on a difference between the frequencies of the system clock and the reference clock over a fixed number of clock cycles of the system clock, adjusting a trim value of the system clock to compensate for the clock error, and disabling the reference clock at an end of the calibration routine. In some examples, the calibration circuitry may include a delta-sigma loop to perform the calibration routine by integrating the clock error over time to calculate a cumulative clock error of the system clock, and adjusting the trim value of the system based on the magnitude and sign of the cumulative clock error. Calibrating the system clock with a delta-sigma loop reduces the clock error over time. This allows accurate adjustment of the system clock to compensate for errors due to trim resolution, circuit noise and temperature. Leadless IMD 16A may include additional calibration circuitry to calibrate other clocks that may be included in leadless IMD 16A, such as a telemetry polling clock and a telemetry linking clock used to operate telemetry between leadless IMD 16A and, e.g., programmer 24 of FIG. 1.

Figure 4:
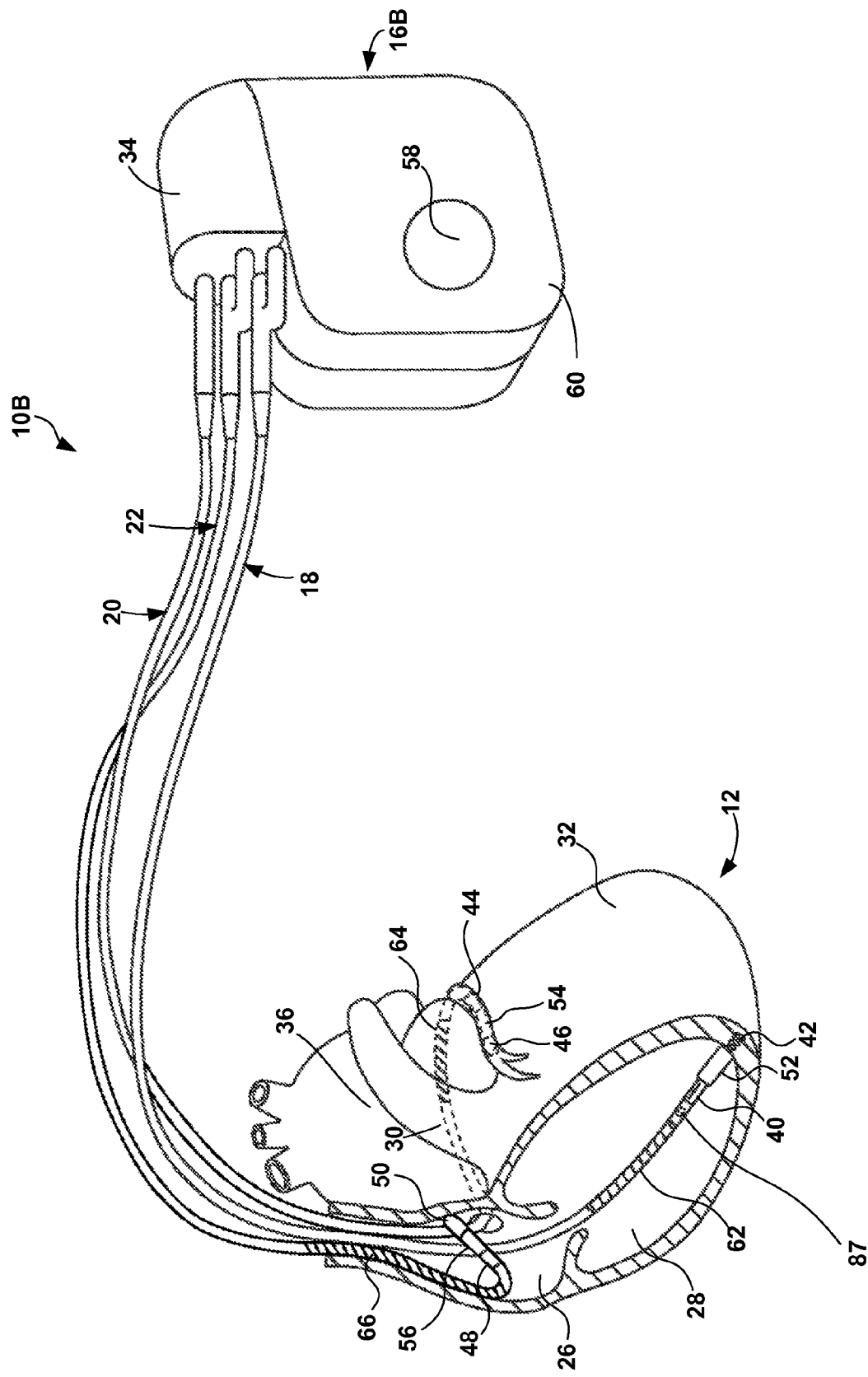
FIG. 4 is a conceptual diagram further illustrating the IMD and leads of the system of FIG. 2 in conjunction with the heart.

FIG. 4 is a conceptual diagram illustrating IMD 16B and leads 18, 20, 22 of therapy system 10B of FIG. 2 in greater detail. Leads 18, 20, 22 may be electrically coupled to a signal generator and a sensing module of IMD 16B via connector block 34. In some examples, proximal ends of leads 18, 20, 22 may include electrical contacts that electrically couple to respective electrical contacts within connector block 34 of IMD 16B. In some examples, a single connector, e.g., an IS-4 or DF-4 connector, may connect multiple electrical contacts to connector block 34. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in left ventricle 32 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In some examples, one or more of electrodes 42, 46, and 50 may take the form of pre-exposed helix tip electrodes. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

In some examples, as illustrated in FIG. 4, IMD 16B includes one or more housing electrodes, such as housing electrode 58, which may be formed integrally with an outer surface of hermetically-sealed housing 60 of IMD 16B or otherwise coupled to housing 60. In some examples, housing electrode 58 is defined by an uninsulated portion of an outward facing portion of housing 60 of IMD 16B. Other division between insulated and uninsulated portions of housing 60 may be employed to define two or more housing electrodes. In some examples, housing electrode 58 comprises substantially all of housing 60.

IMD 16B may sense electrical signals attendant to the depolarization and repolarization of heart 12 via electrodes 40, 42, 44, 46, 48, 50, 58, 62, 64, and 66. The electrical signals are conducted to IMD 16B from the electrodes via conductors within the respective leads 18, 20, 22 or, in the case of housing electrode 58, a conductor coupled to housing electrode 58. IMD 16B may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16B delivers pacing pulses via bipolar combinations of electrodes 40, 42, 44, 46, 48 and 50 to produce depolarization of cardiac tissue of heart 12. In some examples, IMD 16B delivers pacing pulses via any of electrodes 40, 42, 44, 46, 48 and 50 in combination with housing electrode 58 in a unipolar configuration.

Furthermore, IMD 16B may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

IMD 16B also includes a clocking system (not shown in FIG. 4) that includes a system clock, a reference clock, and calibration circuitry. The system clock, according to which IMD 16B performs sensing and therapy delivery, may be a low-power oscillator that suffers from inaccuracies due to poor long-term stability, temperature characteristics, and trim resolution. The reference clock may be a high accuracy oscillator, such as a crystal oscillator, that runs on a substantial amount of current, e.g., between 0.5 and 1 µA. The calibration circuitry periodically performs a calibration routine to calibrate the system clock based on the reference clock. The system clock may be powered continuously to control operation of IMD 16B, but the reference clock may be powered only during the calibration routine to correct inaccuracies of the system clock.

The calibration circuitry may perform the calibration routine according to a calibration period. For example, the calibration circuit may power on the reference clock for approximately 2-3 seconds for each calibration period of approximately 15 minutes to perform the calibration routine. In this way, the total clocking system current drain (including the system clock, the reference clock, and the calibration circuitry) in IMD 16B may be reduced to less than 60 nA.

The calibration circuitry performs the calibration routine by powering on the reference clock at the start of the calibration routine, determining a clock error of the system clock based on a difference between the frequencies of the system clock and the reference clock over a fixed number of clock cycles of the system clock, adjusting a trim value of the system clock to compensate for the clock error, and disabling the reference clock at an end of the calibration routine. In some examples, the calibration circuitry may include a delta-sigma loop to perform the calibration routine by integrating the clock error over time to calculate a cumulative clock error of the system clock, and adjusting the trim value of the system based on the magnitude and sign of the cumulative clock error. Calibrating the system clock with a delta-sigma loop reduces the clock error over time. This allows accurate adjustment of the system clock to compensate for errors due to trim resolution, circuit noise and temperature. IMD 16B may include additional calibration circuitry to calibrate other clocks that may be included in IMD 16B, such as a telemetry polling clock and a telemetry linking clock used to operate telemetry between IMD 16B and, e.g., programmer 24 of FIG. 2.

The configuration of system 10B illustrated in FIGS. 2 and 4 is merely one example. In other examples, a system may include percutaneous leads, epicardial leads and/or patch electrodes instead of or in addition to the transvenous leads 18, 20, 22 illustrated in FIG. 2. Further, IMD 16B need not be implanted within patient 14. In examples in which IMD 16B is not implanted in patient 14, IMD 16B may deliver defibrillation pulses and other therapies to heart 12 via percutaneous leads that extend through the skin of patient 14 to a variety of positions within or outside of heart 12.

Figure 5:
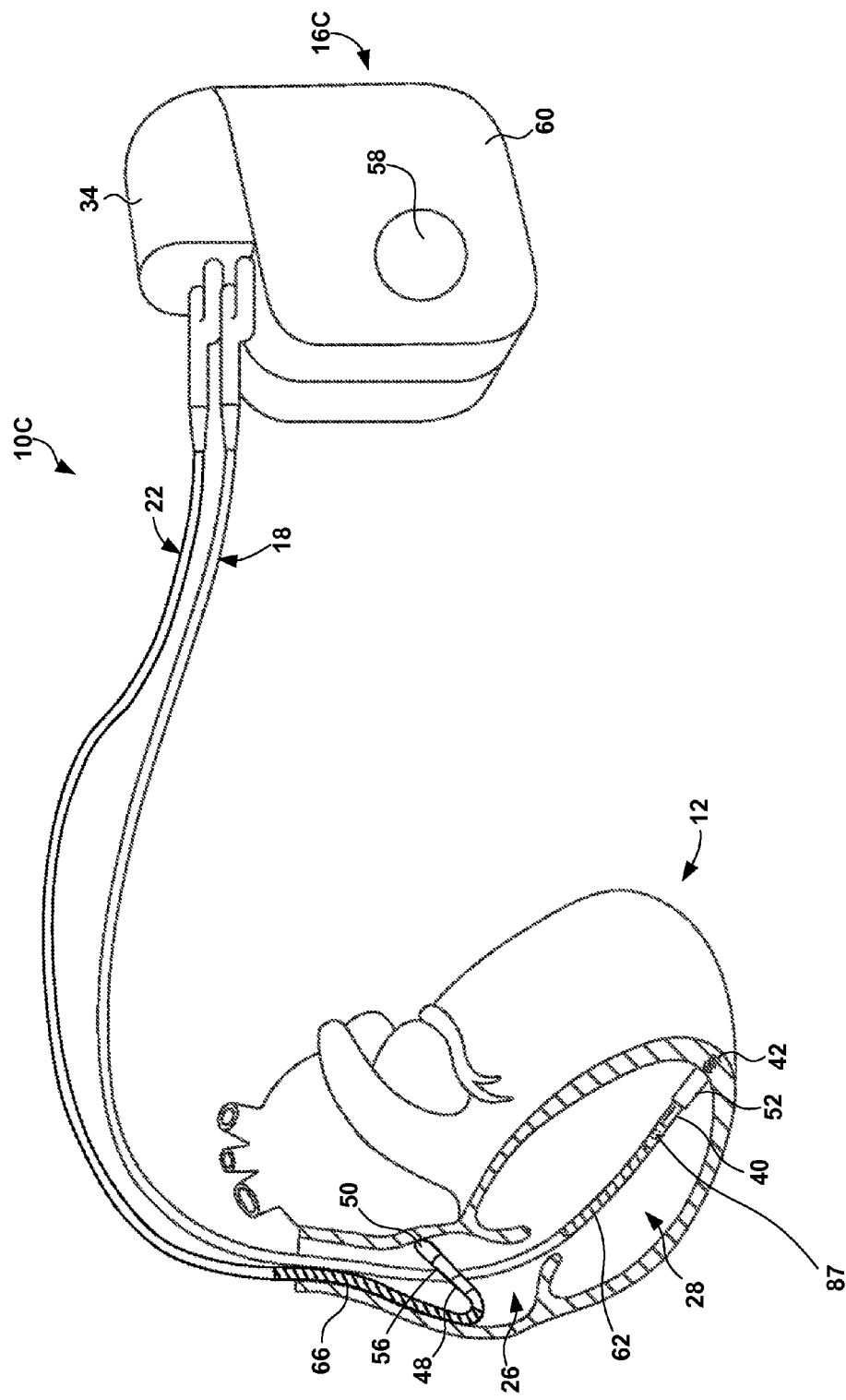
FIG. 5 is a conceptual drawing illustrating the IMD of FIG. 2 coupled to a different configuration of implantable medical leads in conjunction with the heart.

In addition, in other examples, a system may include any suitable number of leads coupled to IMD 16B, and each of the leads may extend to any location within or proximate to heart 12. For example, other examples of systems may include three transvenous leads located as illustrated in FIGS. 2 and 4, and an additional lead located within or proximate to left atrium 36. Other examples of systems may include a single lead that extends from IMD 16B into right atrium 26 or right ventricle 28, or two leads that extend into a respective one of the right ventricle 26 and right atrium 26. An example of this type of system is shown in FIG. 5. Any electrodes located on these additional leads may be used in sensing and/or stimulation configurations.

FIG. 5 is a conceptual diagram illustrating another example system 10C, which is similar to system 10B of FIGS. 2 and 4, but includes two leads 18, 22, rather than three leads. Leads 18, 22 are implanted within right ventricle 28 and right atrium 26, respectively. System 10C shown in FIG. 5 may be useful for physiological sensing and/or providing pacing, cardioversion, or other therapies to heart 12.

As described with respect to IMD 16B of FIGS. 2 and 4, IMD 16C also includes a clocking system (not shown in FIG. 5) that includes a system clock, a reference clock, and calibration circuitry. The system clock, according to which leadless IMD16C performs sensing and therapy delivery, may be a low-power oscillator, and the reference clock may be a high accuracy oscillator. The calibration circuitry periodically performs a calibration routine to calibrate the system clock based on the reference clock. The system clock is powered continuously to control operation of IMD 16C, but the reference clock may be powered only during the calibration routine to correct inaccuracies of the system clock.

Figure 6:
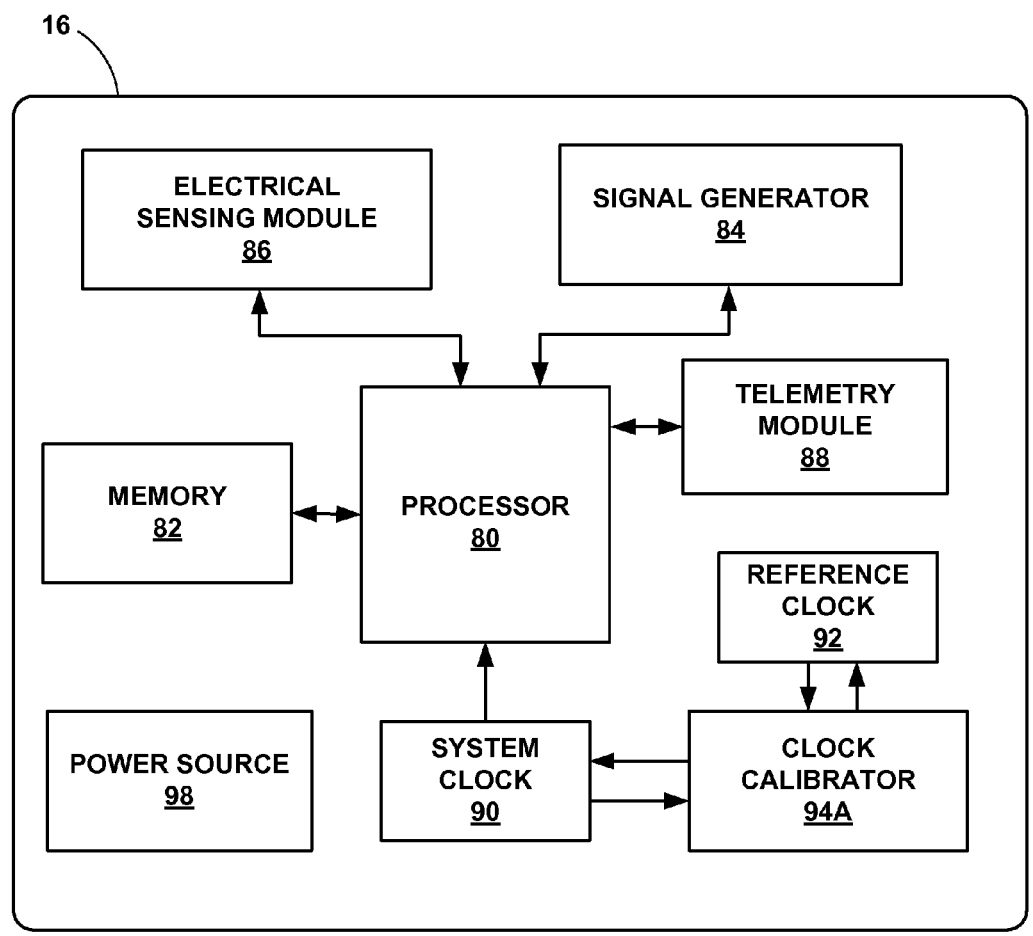
FIG. 6 is a functional block diagram illustrating an example configuration of an IMD.

FIG. 6 is a functional block diagram illustrating an example configuration of IMD 16, which may be 16A of FIGS. 1 and 3 or IMD 16B of FIGS. 2, 4, and 5. In the example illustrated by FIG. 6, IMD 16 includes a processor 80, memory 82, signal generator 84, electrical sensing module 86, telemetry module 88, system clock 90, reference clock 92, clock calibrator 94A, and power source 98. Memory 82 may include computer-readable instructions that, when executed by processor 80, cause IMD 16 and processor 80 to perform various functions attributed to IMD 16 and processor 80 herein. Memory 82 may comprise a computer-readable storage medium, including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog storage media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof. IMD 16 also includes a sensing integrity module 90, as illustrated in FIG. 6, which may be implemented by processor 80, e.g., as a hardware component of processor 80, or a software component executed by processor 80.

Processor 80 controls signal generator 84 to deliver stimulation therapy to heart 12 according to operational parameters or programs, which may be stored in memory 82. For example, processor 80 may control signal generator 84 to deliver electrical pulses with the amplitudes, pulse widths, frequency, or electrode polarities specified by the selected one or more therapy programs.

Signal generator 84, as well as electrical sensing module 86, is electrically coupled to electrodes of IMD 16 and/or leads coupled to IMD 16. In the example of leadless IMD 16A of FIG. 3, signal generator 84 and electrical sensing module 86 are coupled to electrodes 72 and 74, e.g., via conductors disposed within housing 78 of leadless IMD 16A. In examples in which fixation mechanism 70 functions as an electrode, signal generator 84 and electrical sensing module 86 may also be coupled to fixation mechanism 70, e.g., via a conductor disposed within housing 78 of leadless IMD 16A. In the example of IMD 16B of FIG. 4, signal generator 84 and electrical sensing module 86 are coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16B.

In the example illustrated in FIG. 6, signal generator 84 is configured to generate and deliver electrical stimulation therapy to heart 12. For example, signal generator 84 may deliver pacing, cardioversion, defibrillation, and/or neurostimulation therapy via at least a subset of the available electrodes. In some examples, signal generator 84 delivers one or more of these types of stimulation in the form of electrical pulses. In other examples, signal generator 84 may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver stimulation signals, e.g., pacing, cardioversion, defibrillation, and/or neurostimulation signals. The switch module may include a switch array, switch matrix, multiplexer, or any other type of switching device suitable to selectively couple a signal to selected electrodes.

Electrical sensing module 86 monitors signals from at least a subset of the available electrodes in order to monitor electrical activity of heart 12. Electrical sensing module 86 may also include a switch module to select which of the available electrodes are used to sense the heart activity. In some examples, processor 80 may select the electrodes that function as sense electrodes, i.e., select the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chambers of heart 12, and may be configured to detect either R-waves or P-waves. In some examples, electrical sensing module 86 or processor 80 may include an analog-to-digital converter for digitizing the signal received from a sensing channel for electrogram (EGM) signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of the available electrodes appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by signal generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect heart rate, such as an atrial rate or ventricular rate.

Telemetry module 88 includes any suitable hardware, firmware, software or any combination thereof for communicating with another device, such as programmer 24 (FIGS. 1 and 2). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

The clocking system of IMD 16 includes system clock 90, reference clock 92, and clock calibrator 94A. Each of the clocks described herein comprise oscillators that may operate at different frequencies with different accuracies and different power requirements. IMD 16 may require an extremely small housing form factor, especially in the case of leadless IMD 16A of FIGS. 1 and 3. For example, leadless IMD 16 may have a form factor of less than 1 cubic centimeter. Due to the small form factor requirements, IMD 16 may only be able to accommodate a small battery canister such that current drain within IMD 16 must by extremely low. One aspect of reducing power in IMD 16 is to minimize current drain by the clocking system.

In some examples, the clocking system of IMD 16 may include additional clocks not shown in FIG. 6, e.g., a telemetry polling clock, a telemetry linking clock, a CPU clock, and a rate limit clock. A majority of the clocks within the clocking system may be able to operate at a very low duty cycle to minimize power. For example, these clocks may be turned on only when needed and shut down with as close to zero current as possible for the remainder of the time. Since these clocks are powered off most of the time, the average current for the clocks is typically very low even if the current drain required to operate the given clocks is relatively high.

A minimum of one clock, however, must remain continuously enabled to gate sensing and therapy delivery, and to enable other features at certain times. Historically, a high accuracy oscillator, such as a crystal oscillator, has been used as the system clock as it provides a high degree of accuracy (+/−0.01%) at a moderately low current drain. In order to further reduce current drain of the clocking system, a low-power oscillator may be selected as the system clock. Low-power oscillators, however, suffer from inaccuracies due to poor long-term stability, temperature characteristics, and trim resolution.

In accordance with the techniques described herein, system clock 90 is a low-power oscillator that is powered continuously to control operation of IMD 16. Clock calibrator 94A periodically performs a calibration routine to calibrate system clock 90 based on reference clock 92. Reference clock 92 is a high accuracy oscillator, such as a crystal oscillator, that is only powered on during the calibration routine to correct inaccuracies of system clock 90. In some examples, clock calibrator 94A may include a delta-sigma loop to perform the calibration routine. In this case, clock calibrator 94A uses the delta-sigma loop to zero out clock error of system clock 90 in the time-domain, not the frequency domain.

Clock calibrator 94A may perform the calibration routine according to a calibration period, Tcal. In some cases, the calibration period may be set equal to 3.75 minutes, 7.5 minutes, 15 minutes, 30 minutes or 60 minutes. For example, clock calibrator 94A may power on reference clock 92 for approximately 2-3 seconds for each calibration period of approximately 15 minutes to perform the calibration routine. Shorter calibration periods improve accuracy of system clock 90, and longer calibration periods reduce power usage. In some cases, the calibration period may be adjusted to a shorter time period when the frequency of system clock 90 is changing, the temperature is changing, or higher clock accuracy is desired. The calibration routine may be similarly adjusted to a longer time period when the frequency of system clock 90 is stable, the temperature is stable, or less clock accuracy is needed.

Clock calibrator 94A allows a low-power oscillator that is capable of meeting short-term accuracy requirements (+/−1%) to be used as system clock 90, and then periodically powers on a high accuracy oscillator, reference clock 92, to calibrate system clock 90. In this way, clock calibrator 94A is able to improve the long term accuracy of system clock 90 to be comparable to that of reference clock 92. In some examples, clock calibrator 94A is capable of achieving an accuracy goal of keeping track of time to within 15 minutes over a year, i.e., approximately +/−28 ppm (+/−0.0028%). This high level of accuracy is desired when programming therapies to be delivered at specific times of the day or to set a time stamp for when specific events as sensed. Moreover, clock calibrator 94A is further capable of achieving a power goal of reducing total clocking system current drain to less than 60 nA.

Clock calibrator 94A performs the calibration routine by powering on reference clock 92 at the start of the calibration routine, determining a clock error of system clock 90 based on a difference between the frequencies of system clock 90 and reference clock 92 over a fixed number of clock cycles of system clock 90, adjusting a trim value of system clock 90 to compensate for the clock error, and disabling reference clock 92 at an end of the calibration routine. In some examples, clock calibrator 94A may perform the frequency comparison and trim value adjustment once during the calibration routine. In other examples, clock calibrator 94A may perform the frequency comparison and trim value adjustment multiple times during the calibration routine. In some cases, clock calibrator 94A may perform the comparison and adjustment steps a fixed number of times or may continue until a desired accuracy of system clock 90 is reached.

In some examples, clock calibrator 94A uses a calibration routine that adjusts the trim value of system clock 90 by adjusting the trim value by one bit at a time. By only adjusting the trim value by one bit, this calibration routine may respond slowly to a change in frequency of system clock 90 due to temperature, voltage, and drift. In other examples, clock calibrator 94A uses a calibration routine that adjusts the trim value of system clock 90 by adjusting the trim value by more than one bit at a time. This calibration routine would allow system clock 90 to be adjusted more quickly in response to a change in frequency. In either case, the trim value may be incremented or decremented based on whether the clock error indicates that the frequency of system clock 90 is higher or lower than the frequency of reference clock 92.

In another example, clock calibrator 94A may perform the calibration routine with a delta-sigma loop by determining a clock error of system clock 90 based on a difference between the frequencies of system clock 90 and reference clock 92 over a fixed number of clock cycles of system clock 90 (i.e., the delta portion of the delta-sigma loop), integrating the clock error over time to calculate a cumulative clock error of system clock 90 (i.e., the sigma portion of the delta-sigma loop), and adjusting a trim value of system clock 90 to compensate for the cumulative clock error. Calibrating the system clock with a delta-sigma loop reduces the clock error over time. This allows accurate adjustment of the system clock to compensate for errors due to trim resolution, circuit noise and temperature. In this case, the trim value may be increased or decreased based on the magnitude and sign of the cumulative clock error.

As discussed above, reference clock 92 is a high accuracy oscillator, such as a crystal oscillator, that is enabled as necessary to calibrate system clock 90. Reference clock 92 may also be enabled as necessary to calibrate other clocks in the clocking system of IMD 16 (not shown in FIG. 6). Without any trimming or calibration, the accuracy of reference clock 92 may be about +/−50-100 ppm (+/−0.005 to 0.01%). The accuracy of reference clock 92 can be further improved by measuring clock error associated with reference clock 92 at a production test, storing a calibration factor for reference clock 92 into memory 82, and compensating for the clock error when determining time of day. This allows an accuracy of less than +/−5-10 minutes per year or +/−10-20 ppm (+/−0.001 to 0.002%) to be achieved for reference clock 92.

In some examples, reference clock 92 may operate at approximately 32,768 hertz (Hz) and use about 0.5 µA to 1 µA when active. In other examples, reference clock 92 may operate at different frequencies and with different power requirements. Start up time for reference clock 92 is typically slow, e.g., 0.5 to 1 second. Average current drain for reference clock 92 is proportional to the operating current multiplied by its duty cycle (percentage of time reference clock 92 is active). For example, if the duty cycle of reference clock 92 is less than 10%, the current drain associated with reference clock 92 may be reduced by a factor of 10. In accordance with the techniques disclosed herein, clock calibrator 94A may power on reference clock 90 at the start of the calibration routine. Upon power up, reference clock 90 is allowed to stabilize for a period of about 1 second and then run simultaneously with system clock 90 for a fixed number of clock cycles of system clock 90, equivalent to approximately 1-2 seconds. Clock calibrator 94A determines the clock error of system clock 90 based on the difference between the frequencies of system clock 90 and reference clock 92 over the fixed number of clock cycles. Clock calibrator 94A then disables reference clock 92 at the end of the calibration routine. If, for example, reference clock 92 is periodically enabled according to a calibration period, Tcal, equal to 15 minutes, the duty cycle of reference clock 92 is equal to 3 seconds divided by 15 minutes, or 0.333%, such that the average current drain associated with reference clock 92 is reduced from about 1 µA to about 3.3 nA.

As discussed above, system clock 90 may comprise a low-power oscillator that is continuously enabled to operate IMD 16. In some examples, system clock 90 may operate at approximately the same frequency as reference clock 92. For example, system clock 90 may be a 32 kilohertz (kHz) low-power oscillator. In other example, system clock 90 and reference clock 90 may operate a different frequencies. Although system clock 90 suffers from inaccuracies, it may be capable of being trimmed with fine enough resolution to achieve short term accuracy requirements (+/−1%). System clock 90 may also have low enough jitter, temperature coefficient, and supply voltage sensitivity that it can maintain the short term accuracy requirement over the calibration period. The finer the resolution of the trim, the more accurately system clock 90 can be adjusted. In cases where system clock 90 has a fine resolution trim, clock calibrator 94A may perform a less complex calibration routine that adjusts the trim value of system clock 90 by one or more bits at a time. In other cases, clock calibrator 94A may perform a calibration routine with a delta-sigma loop to average out the trim resolution based clock error over time.

System clock 90 may comprise an extremely low power digitally trimmed oscillator, and may be built using an adjustable current, voltage, resistor, capacitor, or number of stages to allow a delay time or clock period of system clock 90 to be adjusted. As one example, system clock 90 may include a digital storage element that sets a value for a programmable value resistor used to generate a bias current. The bias current can be used to adjust delay time of two delay elements. The two delay elements may be configured such that one capacitor in one delay element is being charged up with current, while the other capacitor in the other delay element is being cleared. The two delay elements may create approximately equal delays that are used to define the low and high periods of system clock 90. In accordance with this example, system clock 90 may operate at 32 kHz with a current drain of about 50-100 nA. In other examples, system clock 90 may operate at different frequencies and with different power requirements.

To operate IMD 16, a short term accuracy of approximately +/−1% may be sufficient to meet accuracy requirements over a heart rate pacing cycle or other short term timing requirements. Tighter accuracy of approximately +/−0.35% may be needed over the length of a day to enable or disable sensing and therapies at certain times of the day with an accuracy of approximately +/−5 minutes per day. Moreover, an accuracy equivalent to that of reference clock 92 is required to achieve long term accuracy requirements of keeping track of time to within 5-10 minutes per year.

In accordance with the techniques described herein, the short term accuracy requirements may be achieved by periodically performing a calibration routine to calibrate system clock 90 based on reference clock 92. Clock calibrator 94A periodically determines a clock error of system clock 90 based on a difference in frequencies between system clock 90 and reference clock 92 over a fixed number of clock cycles of system clock 90. Clock calibrator 94A then adjusts a trim value of system clock 90 to compensate for the clock error. In the example of clock calibrator 94A using a calibration routine that adjusts the trim value of system clock 90 by one or more bits at a time, system clock 90 must have a fine resolution trim and clock calibrator 94A may perform the calibration routine more frequently to achieve the accuracy requirements.

In the example of clock calibrator 94A performing the calibration routine with a delta-sigma loop, clock calibrator 94A integrates the clock error over time to calculate a cumulative clock error of system clock 90, and adjusts a trim value of system clock 90 based on the magnitude and sign of the cumulative error until the frequency of system clock 90 is close enough to a target value equal to the frequency of reference clock 92. The medium and long term accuracy requirements may be achieved by keeping track of the average frequency of system clock 90, and adjusting the trim value of system clock 90 to set it to frequencies above and below the target value to maintain an average frequency equal to the target value.

Figure 7:
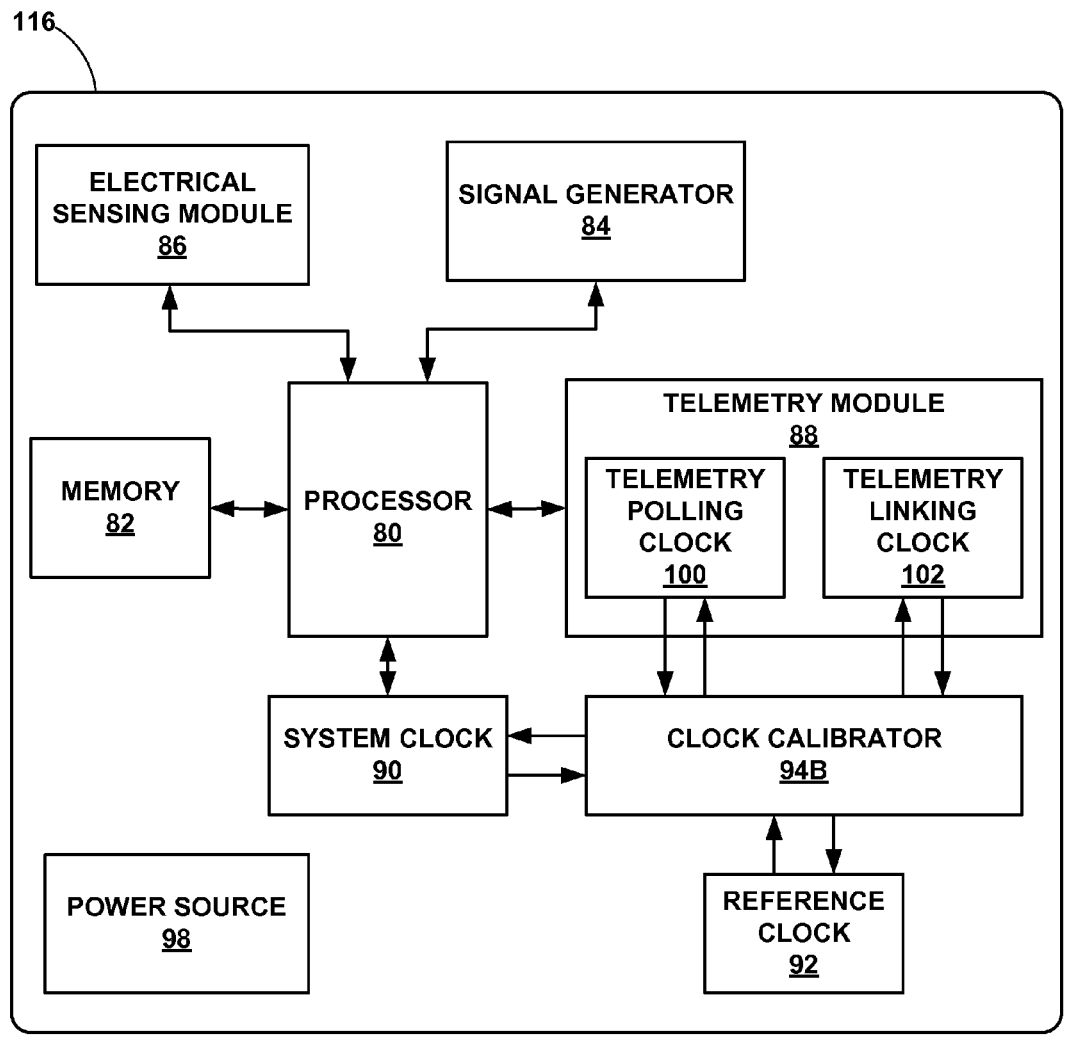
FIG. 7 is a functional block diagram illustrating another example configuration of an IMD.

FIG. 7 is a functional block diagram illustrating an example configuration of IMD 116, which may correspond to IMD 16A of FIGS. 1 and 3 or IMD 16B of FIGS. 2, 4, and 5. IMD 116 may operate substantially similar to IMD 16 of FIG. 6 to perform sensing and therapy delivery to organs or tissue. In the example illustrated by FIG. 7, IMD 116 includes processor 80, memory 82, signal generator 84, electrical sensing module 86, telemetry module 88 with a telemetry polling clock 100 and a telemetry linking clock 102, system clock 90, reference clock 92, a clock calibrator 94B, and power source 98.

IMD 116 may be substantially similar to IMD 16 of FIG. 6 but the clocking system of IMD 116 includes system clock 90, reference clock 92, telemetry polling clock 100, telemetry linking clock 102, and clock calibrator 94B. Telemetry module 88 monitors for a telemetry downlink according to telemetry polling clock 100. Once a telemetry downlink is present, telemetry module 88 performs a telemetry session to communication with, e.g., programmer 24 of FIG. 1 according to telemetry linking clock 102. Clock calibrator 94B may perform substantially similar to clock calibrator 94A of FIG. 6 to perform calibration routines with multiple delta-sigma loops to calibrate system clock 90 and telemetry polling clock 100 and/or telemetry linking clock 102 based on reference clock 92.

Clock calibrator 94B may perform the same type of calibration routine to calibrate all three of the clocks based on reference clock 92. In other cases, clock calibrator 94B may perform different types of calibration routines to calibrate each of the clocks based on reference clock 92. In some examples, clock calibrator 94B may perform a calibration routine with one or more delta-sigma loops. For example, clock calibrator 94B may include three separate delta-sigma loops, one for each clock to be calibrated. Clock calibrator 94B may periodically use two of the delta-sigma loops simultaneously to calibrate system clock 90 and telemetry polling clock 100 based on reference clock 92 according to the same calibration period. Clock calibrator 94B may use the third delta-sigma loop only during a telemetry session to continuously calibrate telemetry linking clock 102 based on reference clock 92.

In accordance with the techniques described herein, telemetry polling clock 100 may comprise a low-power oscillator that is periodically powered to enable and disable a receiver of telemetry module 88 to monitor for the presence of a telemetry downlink. Clock calibrator 94B may periodically perform a calibration routine to simultaneously calibrate system clock 90 and telemetry polling clock 100 according to the same calibration period. For example, clock calibrator 94B may perform the calibration routine using two separate delta-sigma loops to determine clock errors for both system clock 90 and telemetry polling clock 100 over a fixed number of clock cycles of system clock 90 and telemetry polling clock 100, respectively, integrate the clock errors over time to calculate cumulative clock errors, and adjust a trim value of each clock to compensate for the respective cumulative clock errors.

Moreover, telemetry linking clock 102 may comprise a low-power, high frequency oscillator that is powered continuously during a telemetry session to enable telemetry uplink and downlink once a telemetry downlink is present. Clock calibrator 94B periodically calibrates system clock 90 according to the calibration period, and may also periodically calibrate telemetry polling clock 100 according to the same calibration period. In addition, clock calibrator 94B may continuously perform a calibration routine to calibrate telemetry linking clock 102 based on reference clock 92 during the telemetry session. Clock calibrator 94B may power on reference clock 92 at a start of a telemetry session. Clock calibrator 94B may then continuously perform the calibration routine using a third delta-sigma loop during the telemetry session to determine a clock error of telemetry linking clock 102 over a fixed number of clock cycles of the telemetry linking clock 102, integrate the clock error over time to calculate a cumulative clock error, and adjust a trim value of telemetry linking clock 102 to compensate for the cumulative clock error. At the end of the telemetry session, clock calibrator 94B may disable reference clock 92. The calibration routine for telemetry linking clock 102 may be performed continuously during the telemetry session because extremely high clocking accuracy is required to perform telemetry.

As discussed above, telemetry polling clock 100 may comprise a low-power oscillator that is periodically powered to monitor for a telemetry downlink. For example, telemetry polling clock 100 may be enable and disable the telemetry receiver approximately 4 times per second to check for the presence of a telemetry downlink. In some examples, telemetry polling clock 100 may operate at 50 kHz with a current drain of 200 nA. However, telemetry polling clock 100 may only be enabled for 0.5-2 milliseconds (ms) so its duty cycle is less than 0.8%. Therefore, the average current associated with telemetry polling clock 100 is less than 2 nA. In other examples, telemetry polling clock 100 may operate at different frequencies and with different power requirements.

In accordance with the techniques described herein, telemetry polling clock 100 is periodically calibrated whenever system clock 90 is calibrated. The long term accuracy requirements for system clock 90, discussed above, are not as important for telemetry polling clock 100, and therefore a simpler method may be used to determine a trim value of telemetry polling clock 100. In this case, clock calibrator 94B determines a clock error of telemetry polling clock 100 based on a difference between frequencies of telemetry polling clock 100 and reference clock 92 over a fixed number of clock cycles of telemetry polling clock 100 during each calibration routine. The fixed number of clock cycles for the frequency comparison may be equal to 510 clock cycles of telemetry polling clock 100 operating at 50 kHz or 334 clock cycles of reference clock 92 operating at 32,768 Hz, which is approximately 10.2 ms. During each calibration routine, clock calibrator 94B may increment or decrement the trim value of telemetry polling clock 100 by one bit to keep the frequency of telemetry polling clock 100 within +/−0.5% of the target value of 50 kHz. In this example, a separate telemetry polling clock 100 is used to control monitoring for a telemetry downlink because the desired frequency for this function is 50 kHz. In another example, however, system clock 90 may be used to control monitoring for a telemetry downlink if a frequency of 32 kHz is desired.

As discussed above, telemetry linking clock 102 may comprise a low-power, high frequency oscillator that is powered continuously during a telemetry session to enable telemetry uplink and downlink once a telemetry downlink is present. For example, telemetry linking clock 102 may operate at 2.8 MHz with a current drain of approximately 3 μA. In other examples, telemetry linking clock 102 may operate at different frequencies and with different power requirements. The clock accuracy requirements for telemetry uplink are quite tight (approximately +/−0.05% to +/−0.1%). Therefore, in accordance with the techniques described herein, reference clock 92 is continuously enabled during the telemetry session and telemetry linking clock 102 is continuously calibrated based on reference clock 92 during the telemetry session.

More specifically, clock calibrator 94B may continuously determine a clock error of telemetry linking clock 102 based on a difference between frequencies of telemetry linking clock 102 and reference clock 92 over a fixed number of clock cycles of telemetry linking clock 102 during the telemetry session. The fixed number of clock cycles for the frequency comparison may be equal to 1880 clock cycles of telemetry linking clock 102 operating at 2.8 MHz or 22 clock cycles of reference clock 92 operating at 32,768 Hz, which is approximately 671.4 μs. If telemetry linking clock 102 is off by +/−1 clock cycle in error, the trim value of telemetry linking clock 102 is left alone. If telemetry linking clock 102 is off by between +/−2 and +/−27 clock cycles in error, the trim value of telemetry linking clock 102 is adjusted up or down one bit, and then a new frequency comparison is performed. If telemetry linking clock 102 is off by more than +/−28 clock cycles in error, the trim value of telemetry linking clock 102 may be adjusted up or down by a larger step. The trim resolution for telemetry linking clock 102 is nominally 0.05% so moving the trim value by one bit results in a change in the measured number of clock cycles by +/−1 over the fixed number of clock cycles equivalent to 671.4 µs.

In some examples, telemetry linking clock 102 may also be used as a CPU clock to execute instructions. The CPU clock may be enabled once per pacing cycle, or approximately once per second, and remains on for 1-2 ms. Based on this duty cycle, the average current drain of the CPU clock is about 5 nA. The accuracy requirement for executing instructions is not particularly critical. In other examples, once a telemetry downlink is present, telemetry linking clock 102 may be is turned on, divided down, and used in place of telemetry polling clock 100.

The clocking systems of IMD 16 of FIG. 6 and IMD 116 of FIG. 7 may also include a rate limit clock (not shown) that is used as an independent check on heart rate pacing to ensure that a system malfunction did not cause IMD 16 or IMD 116 to pace at an abnormally high rate. In the event that system clock 90 was operating at an abnormally high frequency, the rate limit clock would limit the pacing rate to less than 185 bpm. The rate limit clock is not calibrated based on reference clock 92 in accordance with the techniques described herein. The rate limit clock is also not used for any other functions of IMD 16 or IMD 116. The rate limit clock is continuously enabled and operates at a frequency of approximately 3.2 kHz to minimize current drain.

Figure 8:
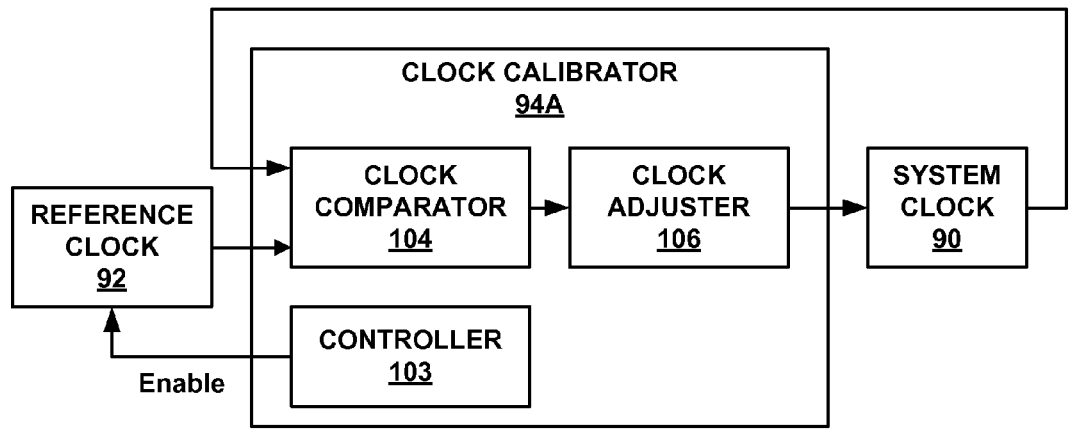
FIG. 8 is a functional block diagram illustrating an example configuration of a clock calibrator included within the IMD of FIG. 6.

FIG. 8 is a functional block diagram illustrating an example configuration of clock calibrator 94A included within IMD 16 of FIG. 6. In the example illustrated by FIG. 8, clock calibrator 94A includes a controller 103 and a delta-sigma loop to calibrate system clock 90 based on reference clock 92. Specifically, the delta-sigma loop includes a clock comparator 104 as the delta portion and a clock adjuster 106 as the sigma portion. System clock 90 and reference clock 92 of IMD 16 are also illustrated in FIG. 8 for purposes of describing the delta-sigma loop. In other example configurations of clock calibrator 94A may not include the delta-sigma loop. In those cases, clock calibrator 94A may simply perform the frequency comparison between system clock 90 and reference clock 92 and then increment or decrement the trim value of system clock 90 by one or more bits.

Clock calibrator 94A periodically performs the calibration routine with the delta-sigma loop to calibrate system clock 90 based on reference clock 92 according to a calibration period. For example, the calibration period, Tcal, may be set equal to 3.75 minutes, 7.5 minutes, 15 minutes, 30 minutes, or 60 minutes. Controller 103 may monitor an amount of time since performing the last calibration routine to determine whether the calibration period has elapsed.

Once the calibration period has elapsed, clock calibrator 94A can perform the calibration routine. At the start of the calibration routine, controller 103 powers on reference clock 92. After it is powered on, reference clock 92 may be allowed to stabilize for approximately 1 second. System clock 90 and reference clock 92 may then run simultaneously over a fixed number of clock cycles of system clock 90. Clock comparator 104 receives the clock signals from system clock 90 and reference clock 92 (Ref Clk) during the calibration routine. Clock comparator 104 then determines a clock error of system clock 90 based on a difference between frequencies of system clock 90 and reference clock 92 over the fixed number of clock cycles. For example, clock comparator 104 may include a system counter clocked by system clock 90 and a reference counter clocked by reference clock 92 such that the difference between the counters over the fixed number of clock cycles of system clock 90 is indicative of the clock error.

Clock adjuster 106 integrates the clock error determined by clock comparator 104 over time to calculate a cumulative clock error of system clock 90. Clock adjuster 106 then adjusts a trim value of system clock 90 to compensate for the cumulative clock error. For example, clock adjuster 106 may increase or decrease the trim value of system clock 90 based on the magnitude and sign of the cumulative clock error. The delta-sigma loop, including clock comparator 104 and clock adjuster 106, reduces the clock error of system clock 90 over time, which allows accurate adjustment of system clock 90 to compensate for errors due to trim resolution, circuit noise and temperature. At the end of the calibration routine, controller 103 disables reference clock 92. Controller 103 may return to monitoring the calibration period to determine when clock calibrator 94A should perform the next calibration routine. In some examples, clock calibrator 94A may perform the frequency comparison and trim value adjustment multiple times during the calibration routine until a desired accuracy of system clock 90 has been reached.

In another example, clock calibrator 94B of FIG. 7 may also include a controller and the delta-sigma loop to calibrate system clock 90. In addition, clock calibrator 94B may include a second delta-sigma loop to calibrate telemetry polling clock 100, and a third delta-sigma loop to calibrate telemetry linking clock 102. The second and third delta-sigma loops may operate substantially similar to the delta-sigma loop for calibrating system clock 90.

In the case of telemetry polling clock 100, clock calibrator 94B may include first and second delta-sigma loops, the first for calibrating system clock 90, as illustrated in FIG. 8, and the second for calibrating telemetry polling clock 100. In this example, clock calibrator 94B may periodically perform a calibration routine to simultaneously calibrate system clock 90 and telemetry polling clock 100 according to the same calibration period. Clock calibrator 94B may perform the calibration routine using both delta-sigma loops to determine clock errors for both system clock 90 and telemetry polling clock 100 over a fixed number of clock cycles of the respective clocks, integrate the clock errors over time to calculate cumulative clock errors, and adjust a trim value of each clock to compensate for the respective cumulative clock errors.

In the case of telemetry linking clock 102, clock calibrator 94B may include the third delta-sigma loop for continuously calibrating telemetry linking clock 102 during a telemetry session. In this example, clock calibrator 94B may continuously perform a calibration routine to calibrate telemetry linking clock 102 based on reference clock 92 during the telemetry session. Clock calibrator 94B may power on reference clock 92 at a start of a telemetry session. Clock calibrator 94B may then continuously perform the calibration routine during the telemetry session to determine a clock error of telemetry linking clock 102 over a fixed number of clock cycles of telemetry linking clock 102, integrate the clock error over time to calculate a cumulative clock error, and adjust a trim value of telemetry linking clock 102 to compensate for the cumulative clock error. At the end of the telemetry session, clock calibrator 94B may disable reference clock 92.

Figure 9:
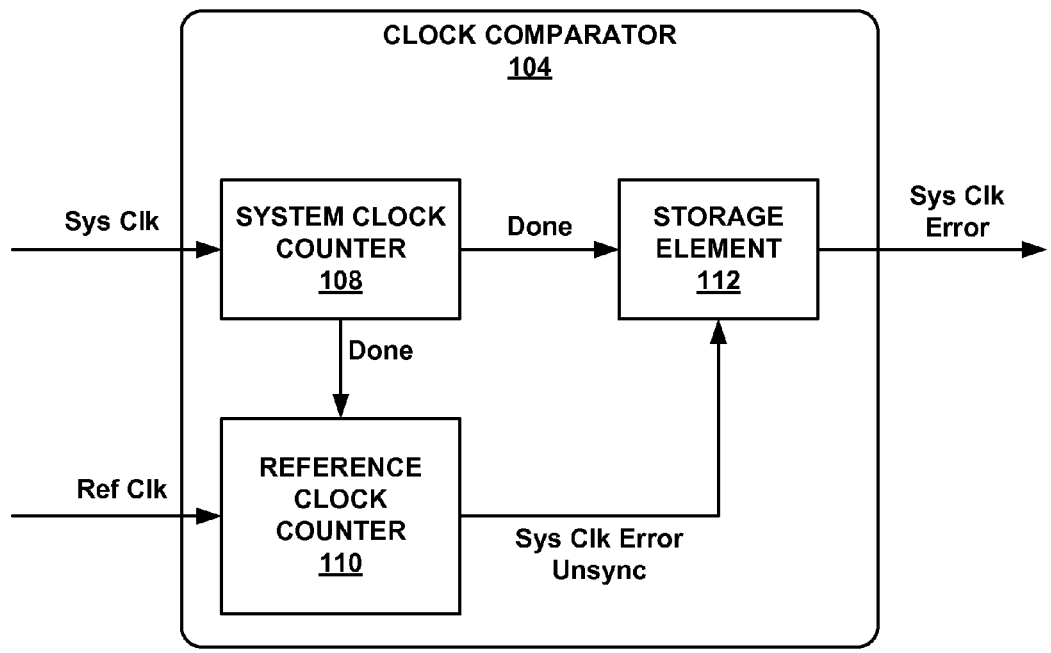
FIG. 9 is a block diagram of an example configuration of a clock comparator of the clock calibrator of FIG. 8.

FIG. 9 is a block diagram of an example configuration of clock comparator 104 of clock calibrator 94A of FIG. 8. In the example illustrated by FIG. 9, clock comparator 104 includes a system clock counter 108, a reference clock counter 110, and a storage element 112. The system clock counter 108 is clocked by system clock 90 (Sys Clk) and reference clock counter 110 is clocked by reference clock 92 (Ref Clk). Both system clock counter 108 and reference clock counter 110 count the number of clock cycles over a fixed number of clock cycles of system clock 90. Clock comparator 104 then determines a clock error of system clock 90 based on the difference between the values of system clock counter 108 and reference clock counter 110 over the fixed number of clock cycles.

In some examples, the fixed number of clock cycles, Ncount, may be equal to $2^{14}$, $2^{15}$, or $2^{16}$. An Ncount of $2^{15}$, or 32,768 clock cycles, is equivalent to the number of clock cycles reference clock 92 operating at 32,768 Hz should be able to perform in 1 second. In other examples, the fixed number of clock cycles may be set equal to any constant value large enough to enable clock comparator 104 get an accurate measurement of the frequency difference between system clock 90 and reference clock 92.

At the start of the calibration routine, system clock counter 108 and reference clock counter 110 are both set equal to the fixed number of clock cycles, Ncount. System clock counter 108 receives a clock signal from system clock 90 (Sys Clk) and decrements by one count for each clock cycle of system clock 90. In a similar fashion, reference clock counter 110 receives a clock signal from reference clock 92 (Ref Clk) and decrements by one count for each clock cycle of reference clock 92.

System clock counter 108 continues to decrement according to system clock 90 until system clock counter 108 reaches zero. Once system clock counter 108 reaches zero, system clock counter 108 notifies system clock counter 108 and storage element 112 that it is done counting. Reference clock counter 110 continues to decrement according to reference clock 92 until reference clock counter 110 receives the done notification from system clock counter 108. Upon receiving the done notification, reference clock counter 110 stops at a reference count value. The reference count value is equal to the difference between the value of system clock counter 108 (i.e., zero) and reference clock counter 110 (i.e., the reference count value) over the fixed number of clock cycles. Therefore, the reference count value is indicative of the clock error of system clock 90.

Storage element 112 synchronizes the clock error of system clock 90 before passing the clock error to clock adjuster 106 (Sys Clk Error). In some examples, storage element 112 may comprise a latch. The final output of clock comparator 104 may be represented by the equation: Sys Clk Error=−(Tref−Tsys)*(Ncount/Tref), where Tref is equal to the transfer function of reference clock 92, Tsys is equal to the transfer function of system clock 90, and Ncount is equal to the fixed number of clock cycles of counters 108 and 110.

In the example described above, system clock counter 108 and reference clock counter are set equal to the same fixed number of clock cycles, Ncount, because system clock 90 and reference clock 92 are assumed to be operating at approximately the same frequency of 32 kHz. In other examples system clock 90 and reference clock 92 may be operating at different frequencies. In that case, system clock counter 108 and reference clock counter 110 may be used in a substantially similar fashion, but one of the counters will initially be set equal to a different value. For example, if system clock 90 is operating at a different frequency, reference clock counter 110 may scale the fixed number of clock cycles by the percentage difference between the operating frequencies of reference clock 92 and system clock 90. As a further example, clock calibrator 94B performs a calibration routine to calibrate telemetry polling clock 100 operating at 50 kHz based on reference clock 92 operating at 32,768 Hz. In the case of telemetry polling clock 100, a polling clock counter may be set equal to Ncount and a reference clock counter may be set equal to 65.5% of Ncount, where 32,768 Hz/50 kHz=0.655. A similar Ncount adjustment would be necessary when calibrating telemetry linking clock 102 operating at 2.8 MHz based on reference clock 92 operating at 32,768 Hz.

Figure 10:
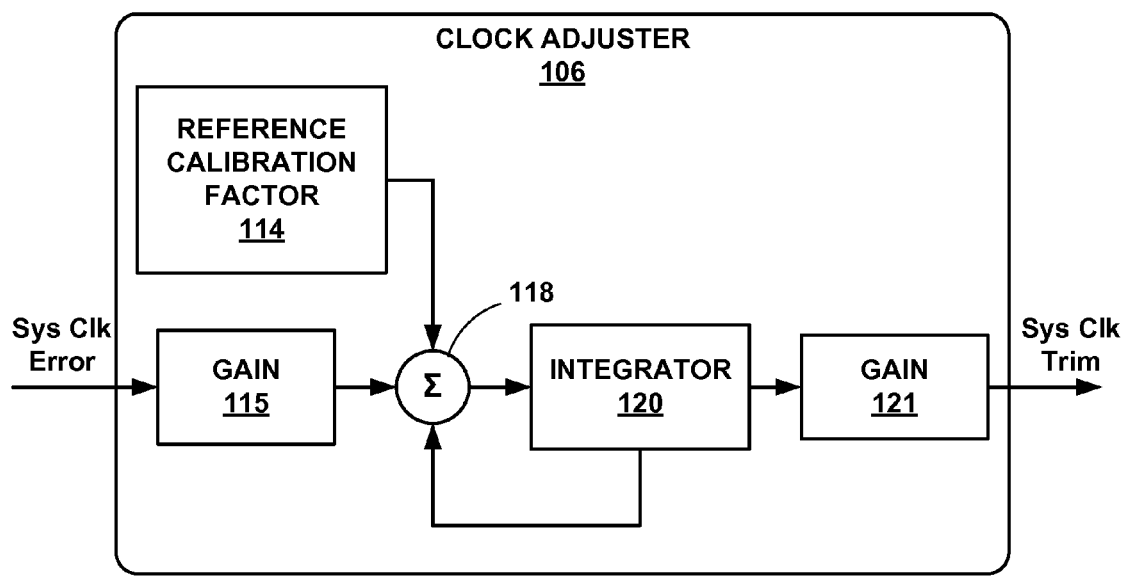
FIG. 10 is a block diagram of an example configuration of a clock adjuster of the clock calibrator of FIG. 8.

FIG. 10 is a block diagram of an example configuration of clock adjuster 106 of clock calibrator 94A of FIG. 8. In the example illustrated by FIG. 10, clock adjuster 106 includes a reference calibration factor 104, gain 115, summer 118, integrator 120, and gain 121. Reference calibration factor 114 is a known value based on a measured clock error of reference clock 92 during a production test and used to compensate for clock error of reference clock 92. Reference calibration factor 114 may be stored directly in clock adjuster 106, or stored in memory 82 of IMD 16 for use by clock adjuster 106. In accordance with the techniques described herein, clock adjuster 106 takes reference calibration factor 114 into account when compensating for the clock error of system clock 90 based on reference clock 92.

Clock adjuster 106 receives the clock error of system clock 90 (Sys Clk Error) from clock comparator 104. Gain 115 performs an arithmetic shift of the clock error value to up-scale the clock error value so summer 118 can add or subtract reference calibration factor 114 to the clock error value. Gain may also perform the arithmetic shift to up-scale the clock error value to compensate for varying values of Ncount. In some examples, gain 115 may up-scale the clock error value by $2^{19}$/Ncount. Summer 118 combines the clock error with reference calibration factor 114 to ensure that all the clock error due to inaccuracies in both system clock 90 and reference clock 92 is compensated. Integrator 120 then integrates the total clock error over time to calculate a cumulative clock error of system clock 90. In some examples, integrator 120 may have an integration function of $Z^{-1}$ or $1/(z-1)$. In other examples, integrator 120 may have a different integration function. Gain 121 may down-scale the cumulative clock error value from integrator 120 to cancel out the effects of the up-scaling by gain 115 and to reduce the overall gain of the delta-sigma loop. In some examples, gain 121 may down-scale the cumulative clock error value by $2^{22}/2^{34}$.

Clock adjuster 106 then outputs a trim value (Sys Clk Trim) for system clock 90 to compensate for the cumulative clock error. For example, clock adjuster 106 may increase or decrease the trim value of system clock 90 based on the magnitude and sign of the cumulative clock error. The delta-sigma loop of clock calibrator 94A reduces the clock error over time, which allows accurate adjustment of the system clock to compensate for errors due to trim resolution, circuit noise and temperature.

The transfer function of clock adjuster 106 may be represented by:

$$\text{Sys Clk Trim} = (\text{gain } 115) * (\text{integrator } 120) * (\text{gain } 121)$$
$$= (2^{19}/N\text{count}) * (1/(z-1)) * (2^{22}/2^{34}),$$

such that Sys Clk Trim=$2^{7}$/(Ncount*(z−1)).

As described above, system clock 90 may include a digital storage element that sets a value for a programmable value resistor used to generate a bias current that is then used to adjust delay time of two delay elements. The two delay elements may be configured such that one capacitor in one delay element is being charged up with current, while the other capacitor in the other delay element is being cleared. The two delay elements create approximately equal delays that are used to define the low and high periods of system clock 90. The delay is set by the relationship T=C*V/I. The clock signal of system clock 90, therefore, may be adjusted by changing the input current to system clock 90. As an example, the transfer function of system clock 90 may be represented by:

$$T_{sys}=1/(2^{15}*(1+80*Sys\ Clk\ Trim)),$$

which may be linearized to the first order and represented as:

$$T_{sys} \approx 2^{-15} - 149n*Sys\ Clk\ Trim$$

Since the offset value of $2^{-15}$ is of little consequence and it makes the transfer function cumbersome, only the dynamic portion may be used and represented as:

$$T_{sys} \approx -150n*Sys\ Clk\ Trim.$$

Furthermore, the overall transfer function of clock calibrator 94A may be represented as:

$$Y=T_{sys}*Sys\ Clk\ Error$$

$$Y=-150n*2^7/(Ncount*(z-1))*-(T_{ref}-T_{sys})*(Ncount/T_{ref})$$

$$Y=150n*2^7*(T_{ref}-T_{sys})/(T_{ref}*(z-1))$$

If Tref is assumed to be a constant equal to $2^{-15}$ and gain is set equal to 1, then:

$$H=1/(z-1)$$

$$Y=T_{ref}*H/(1+H)=1/z$$

Noise Transfer Function $(NTF)=T_{ref}*1/(1+H)=(z-1)/z$

Additionally, in accordance with the techniques described herein, clock calibrator 94A of FIG. 6 and clock calibrator 94B of FIG. 7 may require some storage element support to perform the calibration routines. For example, in the case of clock calibrator 94A, one or more storage elements may be required to hold a trim value of system clock 90, a trim value of reference clock 92, Ncount options (e.g., $2^{14}$, $2^{15}$, $2^{16}$), and Tcal options (e.g., 3.75 min, 7.5 min, 15 min, 30 min, 60 min). Moreover, in the case of clock calibrator 94B, one or more additional storage elements may be required to hold a trim value of telemetry polling clock 100 and a trim value of telemetry linking clock 102.

Figure 11:
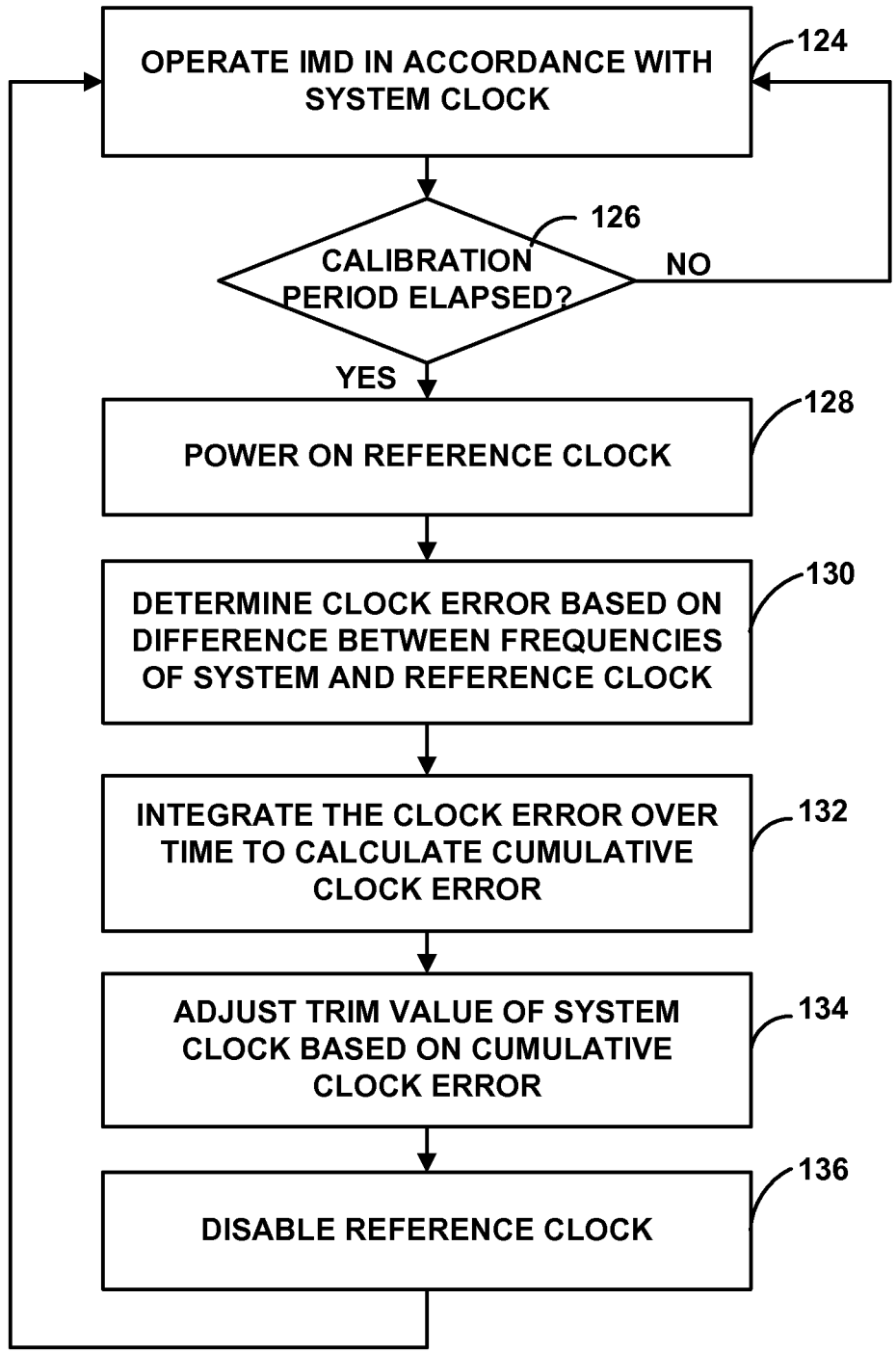
FIG. 11 is a flow diagram of an example method of performing a calibration routine with a delta-sigma loop to calibrate a system clock within the IMD of FIG. 6

FIG. 11 is a flow diagram of an example method of performing a calibration routine with a delta-sigma loop to calibrate a system clock. The example method of FIG. 11 is described as being performed by clock calibrator 94A of FIGS. 6 and 8. As described in more detail below, clock calibrator 94B of FIG. 7 may also implement this method. In other examples, one or more other calibrators or processors may implement all or part of this method.

Processor 80 operates IMD 16 in accordance with system clock 90 (124). For example, processor 80 may control the delivery of stimulation therapy to organs or tissue by signal generator 84 and may control the monitoring of electrical activity of the organs or tissue by electrical sensing module 86 according to the clock cycles of system clock 90.

During operation of IMD 16, controller 103 included in clock calibrator 94A may monitor an amount of time, T, since performing the last calibration routine to determine whether a calibration period, Tcal, has elapsed. In other examples, processor 80 or another processor or device may monitor the calibration period. Clock calibrator 94A periodically performs the calibration routine according to the calibration period. For example, the calibration period, Tcal, may be set equal to 3.75 minutes, 7.5 minutes, 15 minutes, 30 minutes, or 60 minutes.

If the calibration period has not yet elapsed (T≠Tcal) ("no" 126), then processor 80 will continue to operate IMD 16 in accordance with system clock 90 (124). If the calibration period has elapsed (T=Tcal) ("yes" 126), then clock calibrator 94A will perform the calibration routine. At the start of the calibration routine, controller 103 of clock calibrator 94A powers on reference clock 92 (128). After it is powered on, reference clock 92 may be allowed to stabilize for approximately 1 second. System clock 90 and reference clock 92 then run simultaneously over a fixed number of clock cycles of system clock 90. Clock comparator 104 of clock calibrator 94A determines a clock error of system clock 90 based on a difference between frequencies of system clock 90 and reference clock 92 during the fixed number of clock cycles (130). For example, clock comparator 104 may include a system counter clocked by system clock 90 and a reference counter clocked by reference clock 92 such that the difference between the counters over the fixed number of clock cycles is indicative of the clock error.

Clock adjuster 106 of clock calibrator 94A then integrates the clock error determined by clock comparator 104 over time to calculate a cumulative clock error of system clock 90 (132). Clock adjuster 106 then adjusts a trim value of system clock 90 to compensate for the cumulative clock error (134). For example, clock adjuster 106 may increase or decrease the trim value of system clock 90 based on the magnitude and sign of the cumulative clock error. The delta-sigma loop of clock calibrator 94A reduces the clock error over time, which allows accurate adjustment of the system clock to compensate for errors due to trim resolution, circuit noise and temperature.

At the end of the calibration routine, controller 103 of clock calibrator 94A disables reference clock 92 (136). After the calibration routine, processor 80 continues to operate IMD 16 in accordance with system clock 90 as adjusted (124). In addition, controller 103 of clock calibrator 94A returns to monitoring the calibration period (126) to determine when to perform the next calibration routine.

In another example, clock calibrator 94B of FIG. 7 may perform the described method to calibrate system clock 90 based on reference clock 92. Clock calibrator 94B may also perform substantially similar methods of performing calibration routines with delta-sigma loops to calibrate telemetry polling clock 100 and/or telemetry linking clock 102 of telemetry module 88.

In the case of telemetry polling clock 100, clock calibrator 94B may include two delta-sigma loops, one for calibrating system clock 90, as illustrated in FIG. 8, and another for calibrating telemetry polling clock 100. In this example, clock calibrator 94B may periodically perform a calibration routine to simultaneously calibrate system clock 90 and telemetry polling clock 100 according to the same calibration period. Clock calibrator 94B may perform the calibration routine using both delta-sigma loops to determine clock errors for both system clock 90 and telemetry polling clock 100 over a fixed number of clock cycles of each respective clock, integrate the clock errors over time to calculate cumulative clock errors, and adjust a trim value of each clock to compensate for the respective cumulative clock errors.

In the case of telemetry linking clock 102, clock calibrator 94B may include an additional delta-sigma loop for continuously calibrating telemetry linking clock 102 during a telemetry session. In this example, clock calibrator 94B periodically calibrates system clock 90 according to the calibration period, and may also periodically calibrate telemetry polling clock 100 according to the same calibration period. In addition, clock calibrator 94B may continuously perform a calibration routine to calibrate telemetry linking clock 102 based on reference clock 92 during the telemetry session. In this way, clock calibrator 94B may include three separate delta-sigma loops, one for each clock to be calibrated. As discussed above, clock calibrator 94B may periodically use two of the delta-sigma loops simultaneously to calibrate system clock 90 and telemetry polling clock 100 according to the calibration period. Clock calibrator 94B may use the third delta-sigma loop only during a telemetry session to continuously calibrate telemetry linking clock 102.

Clock calibrator 94B may power on reference clock 92 at a start of a telemetry session with, e.g., programmer 24. Clock calibrator 94B may then continuously perform the calibration routine during the telemetry session to determine a clock error of telemetry linking clock 102 over a fixed number of clock cycles of telemetry linking clock 102, integrate the clock error over time to calculate a cumulative clock error, and adjust a trim value of telemetry linking clock 102 to compensate for the cumulative clock error. At the end of the telemetry session, clock calibrator 94B may disable reference clock 92. The calibration routine for telemetry linking clock 102 may be performed continuously during the telemetry session because extremely high clocking accuracy is required to perform telemetry.

Figure 12:
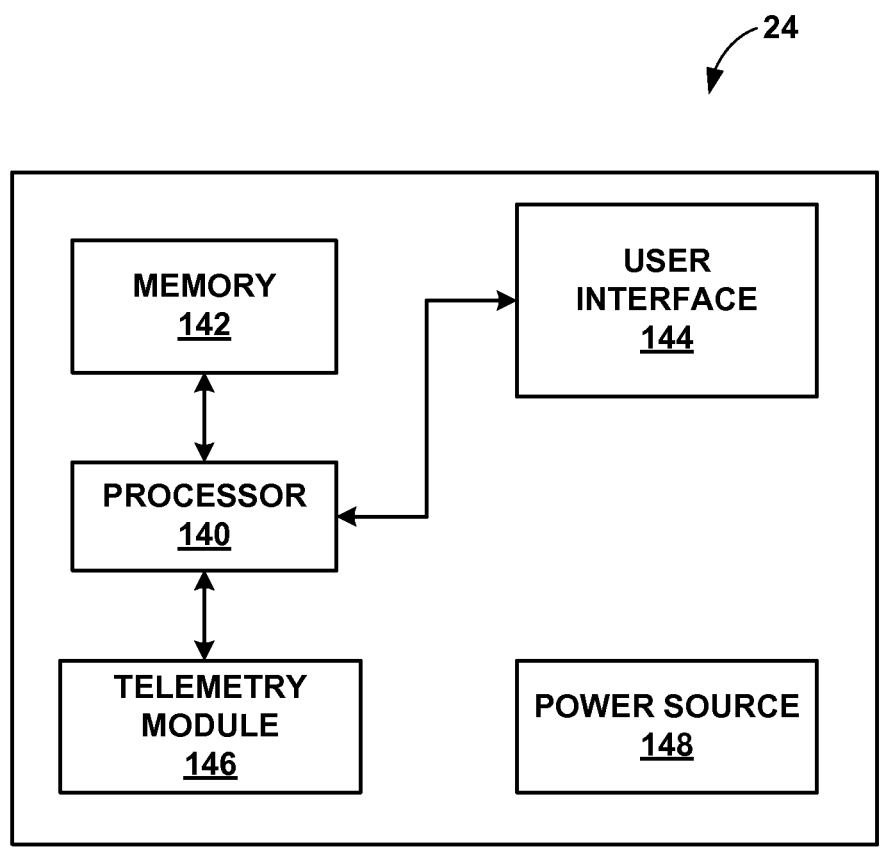
FIG. 12 is a block diagram of an example external programmer that facilitates user communication with an IMD.

FIG. 12 is a functional block diagram of an example configuration of programmer 24. As shown in FIG. 12, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16. In other examples, programmer 24 may be used to program IMD 116 of FIG. 7 in a substantially similar manner as IMD 16 of FIG. 6.

A user may use programmer 24 to select therapy programs (e.g., sets of stimulation parameters), generate new therapy programs, or modify therapy programs for IMD 16. The clinician may interact with programmer 24 via user interface 144, which may include a display to present a graphical user interface to a user, and a keypad or another mechanism for receiving input from a user.

Processor 140 can take the form one or more microprocessors, DSPs, ASICs, FPGAs, programmable logic circuitry, or the like, and the functions attributed to processor 140 in this disclosure may be embodied as hardware, firmware, software or any combination thereof. Memory 142 may store instructions and information that cause processor 140 to provide the functionality ascribed to programmer 24 in this disclosure. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 6).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 of programmer 24 and/or one or more processors of one or more networked computers may perform all or a portion of the techniques described in this disclosure with respect to processor 80 and IMD 16. For example, processor 140 or another processor may receive one or more signals from electrical sensing module 86, or information regarding sensed parameters from IMD 16 via telemetry module 146. In some examples, processor 140 may process or analyze sensed signals, as described in this disclosure with respect to IMD 16 and processor 80. In another example, processor 140 or another processor may transmit one or more signals to IMD 16 to select a different calibration period, Tcal, for clock calibrator 94A. The calibration period may be selected from a group of possible Tcal stored in a storage element associated with clock calibrator 94A, or may be directly specified by a user of programmer 24. Moreover, processor 140 may transmit one or more signals to IMD 16 to select a different fixed number of clock cycles, Ncount, for the clock counters included in clock calibrator 94A. The fixed number of clock cycles may be selected from a group of possible Ncount stored in a storage element associated with clock calibrator 94A, or may be directly specified by a user of programmer 24.

Figure 13:
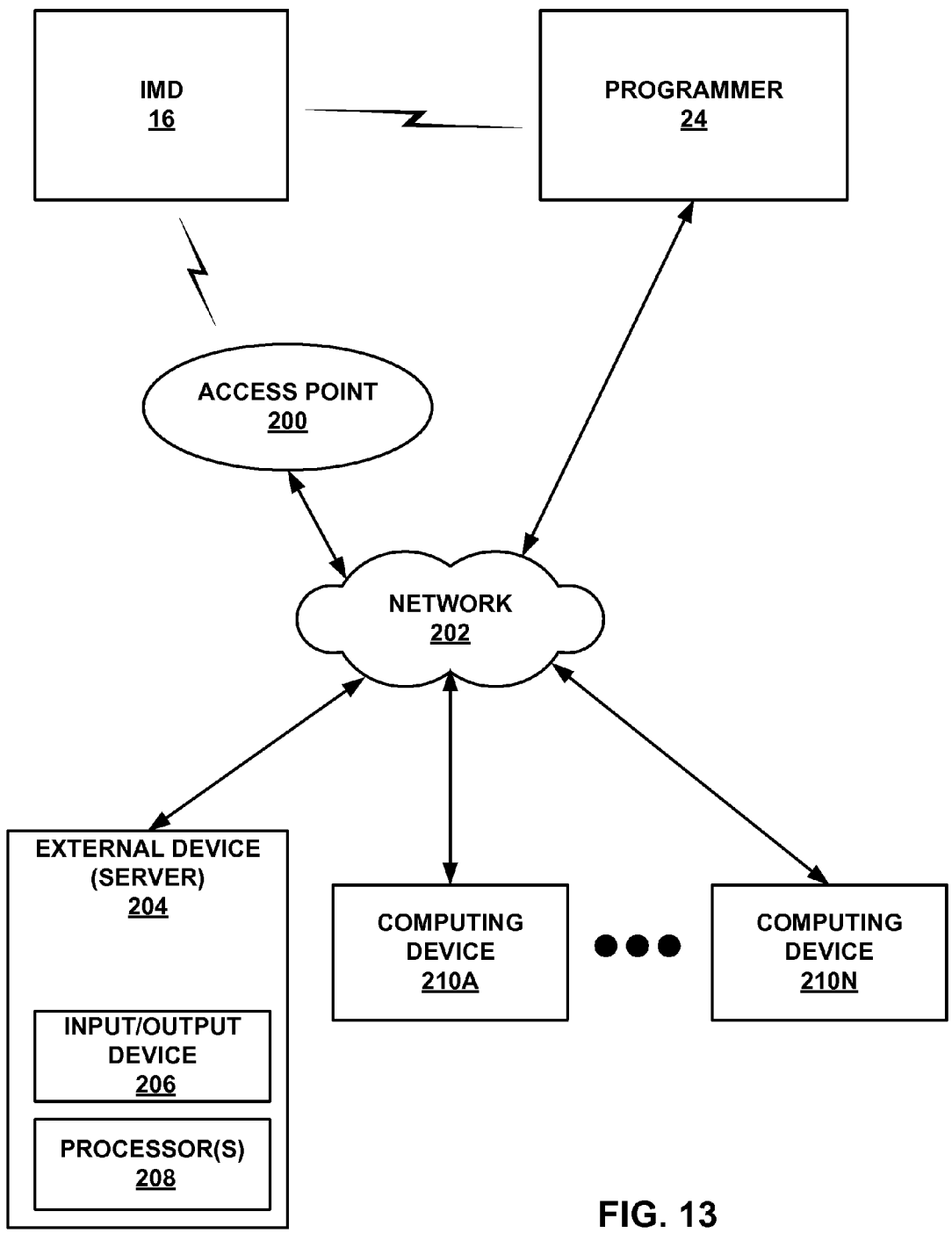
FIG. 13 is a block diagram illustrating an example system that includes an external device, such as a server, and one or more computing devices that are coupled to an IMD and programmer via a network.

FIG. 13 is a block diagram illustrating an example system that includes an external device, such as a server 204, and one or more computing devices 210A-210N, that are coupled to the IMD 16 and programmer 24 (shown in FIGS. 1 and 2) via a network 202. In other examples, the system of FIG. 13 may include IMD 116 of FIG. 7 in a substantially similar manner as IMD 16 of FIG. 6.

In this example, IMD 16 may use its telemetry module 88 to communicate with programmer 24 via a first wireless connection, and to communication with an access point 200 via a second wireless connection. In the example of FIG. 13, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some examples, server 204 or computing devices 210 may control or perform any of the various functions or operations described herein.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 13 may be implemented, in some aspects, with general network technology and functionality similar to that provided by the Medtronic CareLink® Network developed by Medtronic, Inc., of Minneapolis, Minn.

In some examples, processor(s) 208 of server 204 may be configured to provide some or all of the functionality ascribed to IMD 16 and processor 80 herein. For example, processor 208 may receive one or more signals from electrical sensing module 86 or other information regarding sensed parameters from IMD 16 via access point 200 or programmer 24 and network 202. In some examples, server 204 relays received signals provided by one or more of IMD 16 or programmer 24 to one or more of computing devices 210 via network 202. A processor of a computing device 210 may provide some or all of the functionality ascribed to IMD 16 and processor 80 in this disclosure.

In one or more examples, the functions described may be implemented in hardware, software, firmware, or any combination thereof. If implemented in software, the functions may be stored on or transmitted over as one or more instructions or code on a computer-readable medium. Computer-readable media may include computer data storage media or communication media including any medium that facilitates transfer of a computer program from one place to another. Data storage media may be any available media that can be accessed by one or more computers or one or more processors to retrieve instructions, code and/or data structures for implementation of the techniques described in this disclosure. By way of example, and not limitation, such computer-readable media can comprise RAM, ROM, EEPROM, CD-ROM or other optical disk storage, magnetic disk storage, or other magnetic storage devices, flash memory, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

Various examples of the disclosure have been described. These and other examples are within the scope of the following claims.

The invention claimed is:

1. An implantable medical device (IMD) comprising:
a processor;
a system clock that comprises a low power oscillator, according to which the processor operates the IMD;
a reference clock that comprises a high accuracy oscillator; and
a clock calibrator that periodically performs a calibration routine to calibrate the system clock based on the reference clock, wherein the system clock is continuously powered and the reference clock is powered during the calibration routine, wherein the clock calibrator comprises:
a controller that powers on the reference clock at a start of the calibration routine, and disables the reference clock at an end of the calibration routine;
a clock comparator that determines a clock error of the system clock based on a difference between frequencies of the system clock and the reference clock over a fixed number of clock cycles of the system clock, wherein the clock comparator includes:
a system clock counter that is set equal to the fixed number of clock cycles and decrements by one for each clock cycle of the system clock, wherein the system clock counter stops when equal to zero; and
a reference clock counter that is set equal to the fixed number of clock cycles and decrements by one for each clock cycle of the reference clock, wherein the reference clock counter stops at a reference count value when the system clock counter is equal to zero, wherein the reference count value is indicative of the clock error of the system clock; and
a clock adjuster that adjusts a trim value of the system clock to compensate for the clock error.

2. The IMD of claim 1, wherein the clock calibrator performs the calibration routine with a delta-sigma loop, and wherein the clock adjuster integrates the clock error over time to calculate a cumulative clock error of the system clock, and adjusts the trim value of the system clock based on a magnitude and sign of the cumulative clock error.

3. The IMD of claim 1, further comprising:
a telemetry module; and
a telemetry polling clock, according to which the telemetry module monitors for a telemetry downlink,
wherein the clock calibrator periodically performs the calibration routine to simultaneously calibrate the system clock and the telemetry polling clock based on the reference clock.

4. The IMD of claim 1, further comprising:
a telemetry module; and
a telemetry linking clock, according to which the telemetry module performs a telemetry session once a telemetry downlink is present, and wherein the clock calibrator continuously performs a calibration routine to calibrate the telemetry linking clock based on the reference clock during the telemetry session, wherein the reference clock is powered continuously during the telemetry session.

5. The IMD of claim 1, wherein the clock calibrator periodically performs the calibration routine according to a calibration period set equal to one of 3.75 minutes, 7 minutes, 15 minutes, 30 minutes and 60 minutes.

6. The IMD of claim 1, wherein the reference clock comprises a crystal oscillator.

7. An implantable medical device (IMD) comprising: An implantable medical device (IMD) comprising:
a processor;
a system clock that comprises a low power oscillator, according to which the processor operates the IMD;
a reference clock that comprises a high accuracy oscillator; and
a clock calibrator that periodically performs a calibration routine to calibrate the system clock based on the reference clock, wherein the system clock is continuously powered and the reference clock is powered during the calibration routine, wherein the system clock and the reference clock operate at a same clock frequency value.

8. An implantable medical device (IMD) comprising:
a system clock that comprises a low power oscillator;
a reference clock that comprises a high accuracy oscillator;
means for operating the IMD in accordance with the system clock;
means for periodically performing a calibration routine to calibrate the system clock based on the reference clock, wherein the system clock is continuously powered and the reference clock is powered during the calibration routine;
means for powering on the reference clock at a start of the calibration routine;
means for determining a clock error of the system clock based on a difference between frequencies of the system clock and the reference clock over a fixed number of clock cycles of the system clock, wherein means for determining a clock error of the system clock further comprise:
means for setting a system clock counter and a reference clock counter equal to the fixed number of clock cycles;
means for decrementinq the system clock counter by one for each clock cycle of the system clock, wherein the system clock counter stops when equal to zero; and
means for decrementinq the reference clock counter by one for each clock cycle of the reference clock, wherein the reference clock counter stops at a reference count value when the system clock counter is equal to zero, wherein the reference count value is indicative of the clock error of the system clock; and
means for adjusting a trim value of the system clock to compensate for the clock error; and
means for disabling the reference clock at an end of the calibration routine.

9. The IMD of claim 8, wherein means for periodically performing a calibration routine to calibrate the system clock further comprise means for periodically performing a calibration routine with a delta-sigma loop, the IMD further comprising:
means for integrating the clock error over time to calculate a cumulative clock error of the system clock; and
means for adjusting the trim value of the system clock based on a magnitude and sign of the cumulative clock error.

10. The IMD of claim 8, further comprising:
a telemetry polling clock;
means for monitoring for a telemetry downlink in accordance with the telemetry polling clock; and
means for periodically performing the calibration routine to simultaneously calibrate the system clock and the telemetry polling clock based on the reference clock.

11. The IMD of claim 8, further comprising:
a telemetry linking clock;
means for performing a telemetry session in accordance with the telemetry linking clock once a telemetry downlink is present; and
means for continuously performing a calibration routine to calibrate the telemetry linking clock based on the reference clock during the telemetry session, wherein the reference clock is powered continuously during the telemetry session.

12. The IMD of claim 8, wherein means for periodically performing a calibration routine to calibrate the system clock further comprise means for periodically performing the calibration routine according to a calibration period set equal to one of 3.75 minutes, 7 minutes, 15 minutes, 30minutes and 60 minutes.

13. The IMD of claim 8, wherein the reference clock comprises a crystal oscillator.

14. An implantable medical device (IMD) comprising:
a system clock that comprises a low power oscillator;
a reference clock that comprises a high accuracy oscillator;
means for operating the IMD in accordance with the system clock; and
means for periodically performing a calibration routine to calibrate the system clock based on the reference clock, wherein the system clock is continuously powered and the reference clock is powered during the calibration routine, wherein the system clock and the reference clock operate at a same clock frequency value.

* * * * *